(12) United States Patent
Boss et al.

(10) Patent No.: US 9,000,029 B2
(45) Date of Patent: *Apr. 7, 2015

(54) PROLINE SULFONAMIDE DERIVATIVES AS OREXIN RECEPTOR ANTAGONISTS

(71) Applicants: Christoph Boss, Allschwil (CH); Christine Brotschi, Allschwil (CH); John Gatfield, Basel (CH); Markus Gude, Allschwil (CH); Bibia Heidmann, Altkirch (FR); Thierry Sifferlen, Wentzwiller (FR); Jodi T. Williams, Basel (CH)

(72) Inventors: Christoph Boss, Allschwil (CH); Christine Brotschi, Allschwil (CH); John Gatfield, Basel (CH); Markus Gude, Allschwil (CH); Bibia Heidmann, Altkirch (FR); Thierry Sifferlen, Wentzwiller (FR); Jodi T. Williams, Basel (CH)

(73) Assignee: Actelion Pharmaceuticals Ltd., Allschwil (CH)

(*) Notice: Subject to any disclaimer, the term of this patent is extended or adjusted under 35 U.S.C. 154(b) by 0 days.

This patent is subject to a terminal disclaimer.

(21) Appl. No.: 14/530,532

(22) Filed: Oct. 31, 2014

(65) Prior Publication Data

US 2015/0057328 A1 Feb. 26, 2015

Related U.S. Application Data

(63) Continuation of application No. 13/818,647, filed as application No. PCT/IB2011/053693 on Aug. 23, 2011, now Pat. No. 8,895,606.

(30) Foreign Application Priority Data

Aug. 24, 2010 (WO) ............... PCT/IB2010/053799

(51) Int. Cl.
*A61K 31/40* (2006.01)
*C07D 207/48* (2006.01)

(52) U.S. Cl.
CPC .................... *C07D 207/48* (2013.01)

(58) Field of Classification Search
USPC ........................................ 514/422
See application file for complete search history.

(56) References Cited

U.S. PATENT DOCUMENTS

| | | | |
|---|---|---|---|
| 4,217,130 A | 8/1980 | Tsuruta et al. |
| 6,291,453 B1 | 9/2001 | Ashwell et al. |
| 6,410,561 B1 | 6/2002 | Shinkai et al. |
| 7,288,538 B2 | 10/2007 | Wu et al. |
| 7,319,111 B2 | 1/2008 | Gao et al. |
| 7,579,340 B2 | 8/2009 | Biediger et al. |
| 7,763,638 B2 | 7/2010 | Aissaoui et al. |
| 7,998,959 B2 | 8/2011 | Yao et al. |
| 8,642,660 B2 | 2/2014 | Goldfarb |
| 2003/0176465 A1 | 9/2003 | Mederski et al. |
| 2007/0191424 A1 | 8/2007 | Aissaoui et al. |
| 2009/0082394 A1 | 3/2009 | Jenck |
| 2009/0163545 A1 | 6/2009 | Goldfarb |
| 2009/0291947 A1 | 11/2009 | Shao et al. |
| 2010/0029736 A1 | 2/2010 | Cox et al. |
| 2010/0234420 A1 | 9/2010 | Jenck |
| 2013/0150424 A1 | 6/2013 | Boss et al. |

FOREIGN PATENT DOCUMENTS

| | | |
|---|---|---|
| EP | 2 447 249 A1 | 5/2012 |
| EP | 2 452 934 A1 | 5/2012 |
| JP | 55-81857 | 6/1980 |
| WO | WO 99/48492 A1 | 9/1999 |
| WO | WO 02/06269 A1 | 1/2002 |
| WO | WO 2004/041807 A1 | 5/2004 |
| WO | WO 2004/073634 A2 | 9/2004 |
| WO | WO 2005/061475 A2 | 7/2005 |
| WO | WO 2005/118548 A1 | 12/2005 |
| WO | WO 2006/022442 A1 | 3/2006 |
| WO | WO 2006/133326 A1 | 12/2006 |
| WO | WO 2007/084314 A2 | 7/2007 |
| WO | WO 2007/105177 A1 | 9/2007 |
| WO | WO 2009/047723 A2 | 4/2009 |
| WO | WO 2009/086303 A2 | 7/2009 |
| WO | WO 2010/077836 A2 | 7/2010 |
| WO | WO 2010/149820 A1 | 12/2010 |

(Continued)

OTHER PUBLICATIONS

Adam, T. et al., "Stress, Eating and the Reward System," Physiology and Behavior, 2007, 91 (4), 449-458.

(Continued)

*Primary Examiner* — Wu-Cheng Winston Shen
*Assistant Examiner* — Christopher R Stone
(74) *Attorney, Agent, or Firm* — Hoxie & Associates LLC

(57) ABSTRACT

The present invention relates to (S)-proline sulfonamide compounds of formula (I)

Formula (I)

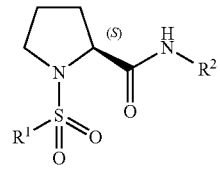

wherein $R^1$ and $R^2$ are as described in the description, or pharmaceutically acceptable salts thereof, for use in the prevention or treatment of diseases or disorders related to the orexin system. The present invention also relates to the use of (S)-proline sulfonamide compounds of formula (II) as pharmaceuticals, to pharmaceutical compositions comprising compounds of formula (II), and especially their use in the prevention or treatment of diseases or disorders related to the orexin system.

13 Claims, 2 Drawing Sheets

(56) References Cited

FOREIGN PATENT DOCUMENTS

| WO | WO 2010/150205 A1 | 12/2010 |
|---|---|---|
| WO | WO 2011/000993 A1 | 1/2011 |

OTHER PUBLICATIONS

Aston-Jones, G. et al., "Lateral Hypothalamic Orexin/Hypocretin Neurons: A Role in Reward-Seeking and Addiction," Brain Research, 2009, doi:10.1016/j.brainres.2009.09.106 (uncorrected proof), 18 pages.
Berridge, C. et al., "Hypocretin/Orexin in Arousal and Stress," Brain Research, NIH Public Access, Author Manuscript, available in PMC Feb. 16, 2011, 21 pages, published in final edited form as Brain Research, 2010, 1314, 91-102.
Borgland, S. et al., "Orexin A in the VTA Is Critical for the Induction of Synaptic Plasticity and Behavioral Sensitization to Cocaine," Neuron, 2006, 49 (4), 589-601.
Boss, C. et al., "Biomedical Application of Orexin/Hypocretin Receptor Ligands in Neuroscience," Journal of Medicinal Chemistry, 2009, 52 (4), 891-903.
Boutrel, B. et al., "Role for Hypocretin in Mediating Stress-Induced Reinstatement of Cocaine-Seeking Behavior," Proceedings of the National Academy of Sciences, 2005, 102 (52), 19168-19173.
Brisbare-Roch, C. et al., "Promotion of Sleep by Targeting the Orexin System in Rats, Dogs and Humans," Nature Medicine, published online Jan. 28, 2007, doi:10.1038/nm1544, 6 pages.
Cai, J. et al., "Antagonists of the Orexin Receptors," Expert Opinion on Therapeutic Patents, 2006, 16(5), 631-646.
Carter, M. et al, "The Brain Hypocretins and Their Receptors: Mediators of Allostatic Arousal," Current Opinion in Pharmacology, 2009, doi:10.1016/j.coph.2008.12.018, 7 pages.
Chang, L. et al., "Highly Constrained Bicyclic VLA-4 Antagonists," Bioorganic and Medicinal Chemistry Letters, 2007, 17 (3), 597-601.
Chemelli, R. et al., "Narcolepsy in *orexin* Knockout Mice: Molecular Genetics of Sleep Regulation," Cell, 1999, 98, 437-451.
Chrousos, G. et al., "The Concepts of Stress and Stress System Disorders," JAMA, 1992, 267 (9), 1244-1252.
Desarnaud, F. et al., "The Diurnal Rhythm of Hypocretin in Young and Old F344 Rats," Sleep, 2004, 27 (5), 851-856.
Dietrich, H. et al., "Intact Learning and Memory in Rats Following Treatment with Dual Orexin Receptor Antagonist Almorexant," Psychopharmacology, 2010, 212, 145-154.
English-language abstract from the European Patent Office website for JP 55-81857, http://worldwide.espacenet.com/publicationDetails/biblio?DB=EPODOC&II=0&ND=4&adjacent=true&locale=en_EP&FT=D&date=19800620&CC=JP&NR=S5581857A&KC=A, website accessed Feb. 21, 2014, 2 pages.
Fendt, M. et al., "The Neuroanatomical and Neurochemical Basis of Conditioned Fear," Neuroscience and Biobehavioral Reviews, 1999, 23, 743-760.
Feng, P. et al., "Changes in Brain Orexin Levels in a Rat Model of Depression Induced by Neonatal Administration of Clomipramine," Journal of Psychopharmacology, 2008, 22 (7), 784-791.
Furlong, T. et al., "Hypocretin/Orexin Contributes to the Expression of Some But Not All Forms of Stress and Arousal," European Journal of Neuroscience, 2009, doi:10.1111/j.1460-9568.2009.06952.x, 12 pages.
Gennaro, A., Ed., Remington: The Science and Practice of Pharmacy, 20th Edition, Philadelphia College of Pharmacy and Science, 2001.
Georgescu, D. et al., "Involvement of the Lateral Hypothalamic Peptide Orexin in Morphine Dependence and Withdrawal," The Journal of Neuroscience, 2003, 23 (8), 3106-3111.
Gibson, M., Ed., Pharmaceutical Preformulation and Formulation, A Practical Guide from Candidate Drug Selection to Commercial Dosage Form, IHS Health Group, A CRC Press Book, Englewood, CO, USA, 2001, ISBN: 1574911201.
Gould, P., "Salt Selection for Basic Drugs," International Journal of Pharmaceutics, 1986, 33, 201-217.
Gozzi, A. et al., "Functional Magnetic Resonance Imaging Reveals Different Neural Substrates for the Effects of Orexin-1 and Orexin-2 Receptor Antagonists," PLoS One, 2011, 6(1), e16406, doi:10.1371/journal.pone.0016406, 12 pages.
Harris, G. et al., "A Role for Lateral Hypothalamic Orexin Neurons in Reward Seeking," Nature, 2005, 437 (7058), 556-559.
Hollander, J. et al., "Insular Hypocretin Transmission Regulates Nicotine Reward," Proceedings of the National Academy of Sciences, 2008, 105 (49), 19479-19484.
Hutcheson, D. et al., "Orexin-1 Receptor Antagonist SB-334867 Reduces the Acquisition and Expression of Cocaine-Conditioned Reinforcement and the Expression of Amphetamine-Conditioned Reward," Behavioural Pharmacology, 2011, doi:10.1097/FBP.0b013e328343d761, 9 pages.
International Preliminary Report on Patentability for International Application No. PCT/IB2011/053693, date of issuance Feb. 26, 2013, 9 pages.
International Search Report for International Application No. PCT/IB2011/053693 mailed Dec. 2, 2011, 4 pages.
Kane, J. et al., "Nicotine Up-Regulates Expression of Orexin and its Receptors in Rat Brain," Endocrinology, 2000, 141 (10), 3623-3629.
Kang, J. et al., "Amyloid-β Dynamics Are Regulated by Orexin and the Sleep-Wake Cycle," Sciencexpress, 2009, doi:10.1126/science.1180962, 8 pages.
Kayaba, Y. et al., "Attenuated Defense Response and Low Basal Blood Pressure in Orexin Knockout Mice," American Journal of Physiology—Regulatory, Integrative, and Comparative Physiology, 2003, 285, R581-R593.
Kiwaki, K. et al., "Orexin A (Hypocretin 1) Injected into Hypothalamic Paraventricular Nucleus and Spontaneous Physical Activity in Rats," American Journal of Physiology—Endocrinology and Metabolism, 2004, 286 (4), E551-E559.
Kiyashchenko, L. et al., "Release of Hypocretin (Orexin) During Waking and Sleep States," The Journal of Neuroscience, 2002, 22 (13), 5282-5286.
Koob, G. et al., "Neurobiological Mechanisms of Addiction: Focus on Corticotropin-Releasing Factor," Current Opinion in Investigational Drugs, 2010, 11 (1), 63-71.
Lawrence, A. et al., "The Orexin System Regulates Alcohol-Seeking in Rats," British Journal of Pharmacology, 2006, 148 (6), 752-759.
Lee, M. et al., "Discharge of Identified Orexin/Hypocretin Neurons Across the Sleep-Waking Cycle," The Journal of Neuroscience, 2005, 25 (28), 6716-6720.
Lesage, M. et al., "Nicotine Self-Administration in the Rat: Effects of Hypocretin Antagonists and Changes in the Hypocretin mRNA," Psychopharmacology, 2010, 209 (2), 203-212.
Liu, X., et al., "Insomnia and Hypersomnia Associated with Depressive Phenomenology and Comorbidity in Childhood Depression," Sleep, 2007, 30 (1), 83-90.
Majzoub, J., "Corticotropin-Releasing Hormone Physiology," European Journal of Endocrinology, 2006, 155 (suppl 1), S71-S76.
Mathes, W. et al., "The Biology of Binge Eating," Appetite, 2009, 52, 545-553.
Mileykovskiy, B. et al., "Behavioral Correlates of Activity in Identified Hypocretin/Orexin Neurons," Neuron, 2005, 46 (5), 787-798.
Narita, M. et al., "Direct Involvement of Orexinergic Systems in the Activation of the Mesolimbic Dopamine Pathway and Related Behaviors Induced by Morphine," The Journal of Neuroscience, 2006, 26 (2), 398-405.
Nollet, M. et al., "Activation of Orexin Neurons in Dorsomedial/Perifornical Hypothalamus and Antidepressant Reversal in a Rodent Model of Depression," Neuropharmacology, 2011, doi:10.1016/j.neuropharm.2011.04.022, 11 pages.
Piper, D. et al., "The Novel Brain Neuropeptide, Orexin-A, Modulates the Sleep-Wake Cycle of Rats," European Journal of Neuroscience, 2000, 12 (2), 726-730.
Prud'Homme, M. et al., "Nutritional Status Modulates Behavioural and Olfactory Bulb Fos Responses to Isoamyl Acetate or Food Odour in Rats: Roles of Orexins and Leptin," Neuroscience, 2009, 162 (4), 1287-1298.
PubChem Compound Summary for: CID 16828035, AGN-PC-016WCG, Create Date: Nov. 13, 2007, 4 pages, retrieved on Apr. 23, 2014.

(56) References Cited

OTHER PUBLICATIONS

PubChem ZINC09068446—Compound Summary (CID 40924317), Create Date: May 30, 2009, 2 pages, retrieved on Sep. 1, 2011.
PubChem Compound Summary for: CID 40924321, ZINC09068450, Create Date: May 30, 2009, 4 pages, retrieved on Apr. 23, 2014.
PubChem BioAssay: AID 434989, Deposit Date: Jun. 15, 2010, 7 pages, retrieved on Apr. 23, 2014.
PubChem BioAssay: AID 504701, Deposit Date: Apr. 22, 2011, 8 pages retrieved on Apr. 23, 2014.
PubChem MLS002247905—Substance Summary, Chemical Structure (CID 2315573), Deposited Record (SID 85268585), Deposit Date: Nov. 5, 2009, Modify Date: Nov. 5, 2009, 2 pages, retrieved on Sep. 14, 2011.
PubChem MLS001076936—Substance Summary, Chemical Structure (CID 20880646), Deposited Record (SID 49718691), Deposit Date: May 21, 2008, Modify Date: May 21, 2008, 2 pages, retrieved on Sep. 14, 2011.
PubChem MLS001223988—Substance Summary, Chemical Structure (CID 3228462), Deposited Record (SID 49727331), Deposit Date: May 21, 2008, Modify Date: May 21, 2008, 2 pages, retrieved on Sep. 14, 2011.
PubChem MLS002166024—Substance Summary, Chemical Structure (CID 4879906), Deposited Record (SID 57262856), Deposit Date: Feb. 23, 2009, Modify Date: Feb. 23, 2009, 2 pages, retrieved on Sep. 14, 2011.
PubChem MLS000937074—Substance Summary, Chemical Structure (CID 22429402), Deposited Record (SID 49715682), Deposit Date: May 21, 2008, Modify Date: May 21, 2008, 2 pages, retrieved on Sep. 14, 2011.
PubChem MLS00531786—Substance Summary, Chemical Structure (CID 2961359), Deposited Record (SID 14736873), Deposit Date: Oct. 20, 2006, Modify Date: Feb. 10, 2007, 2 pages, retrieved on Sep. 14, 2011.
PubChem Compound Summary for: CID 651337, 1-(4-Methoxybenzenesulfonyl)-pyrrolidine-2-carboxylic acid p-tolyamide, Create Date: Jun. 4, 2005, 3 pages, retrieved on Mar. 13, 2014.
PubChem Compound Summary for: CID 2937052, F1475-0198, Create Date: Jul. 29, 2005, 3 pages, retrieved on Mar. 13, 2014.
PubChem Compound Summary for: CID 2948105, ST50102148, Create Date: Jul. 29, 2005, 3 pages, retrieved on Mar. 13, 2014.
Quarta, D. et al., "The Orexin-1 Receptor Antagonist SB-334867 Reduces Amphetamine-Evoked Dopamine Outflow in the Shell of the Nucleus Accumbens and Decreases the Expression of Amphetamine Sensitization," Neurochemistry International, 2009, doi:10.1016/j.neuint.2009.08.012 (uncorrected proof), 5 pages.
Sakurai, T. et al., "Orexins and Orexin Receptors: A Family of Hypothalamic Neuropeptides and G Protein-Coupled Receptors that Regulate Feeding Behavior," Cell, 1998, 92, 573-585.
Salomon, R. et al., "Diurnal Variation of Cerebrospinal Fluid Hypocretin-1 (Orexin-A) Levels in Control and Depressed Subjects," Biological Psychiatry, 2003, 54 (2), 96-104.
Samson, W. et al., "Orexin Receptor Subtype Activation and Locomotor Behavior in the Rat," Acta Physiologica, NIH Public Access, Author Manuscript, available in PMC Mar. 1, 2011, 33 pages, published in final edited form as Acta Physiologica, 2010, 198 (3), 313-324.
Sharf, R. et al., "Role of Orexin/Hypocretin in Dependence and Addiction," Brain Research, 2010, 1314, 130-138.
Shippenberg, T. et al., Chapter 97, "Recent Advances in Animal Models of Drug Addiction," 2002, pp. 1381-1397 in Neuropsychopharmacology: The Fifth Generation of Progress, Davis, K. et al., Eds., 2002.
Smith, R. et al., "Orexin/Hypocretin Signaling at the $OX_1$ Receptor Regulates Cue-Elicited Cocaine-Seeking," European Journal of Neuroscience, NIH Public Access, Author Manuscript, available in PMC Aug. 1, 2010, 21 pages, published in final edited form as European Journal of Neuroscience, 2009, 30 (3), 493-503.
Smith, R. et al., "Orexin/Hypocretin is Necessary for Context-Driven Cocaine-Seeking," Neuropharmacology, NIH Public Access, Author Manuscript, available in PMC Jan. 1, 2011, 14 pages, published in final edited form as Neuropharmacology, 2010, 58 (1), 179-184.
Spealman, R. et al., "Pharmacological and Environmental Determinants of Relapse to Cocaine-Seeking Behavior," Pharmacology Biochemistry and Behavior, 1999, 64 (2), 327-336.
Stickgold, R., "Sleep-Dependent Memory Consolidation," Nature, 2005, 437 (7063), 1272-1278.
Sutcliffe, J. et al., "The Hypocretins: Setting the Arousal Threshold," Nature Reviews, Neuroscience, 2002, 3 (5), 339-349.
Tsujino, N. et al., "Orexin/Hypocretin: A Neuropeptide at the Interface of Sleep, Energy Homeostasis and Reward System," Pharmacological Reviews, 2009, 61 (2), 162-176.
Vanderschuren, L. et al., "Sensitization Processes in Drug Addiction," Current Topics in Behavioral Neurosciences, Behavioral Neuroscience of Drug Addiction, 2009, 3, 179-195.
Vinkers, C. et al., "Translational Aspects of Pharmacological Research into Anxiety Disorders: The Stress-Induced Hyperthermia (SIH) Paradigm," European Journal of Pharmacology, 2008, 585, 407-425.
Winrow, C. et al., "Orexin Receptor Antagonism Prevents Transcriptional and Behavioral Plasticity Resulting from Stimulant Exposure," Neuropharmacology, 2009, doi:10.1016/j.neuropharm.2009.07.008 (uncorrected proof), 10 pages.
Zeitzer, J. et al., "Circadian and Homeostatic Regulation of Hypocretin in a Primate Model: Implications for the Consolidation of Wakefulness," The Journal of Neuroscience, 2003, 23 (8), 3555-3560.
Zhang, G. et al., "Long-Lasting Up-Regulation of Orexin Receptor Type 2 Protein Levels in the Rat Nucleus Accumbens After Chronic Cocaine Administration," Journal of Neurochemistry, 2007, 103 (1), 400-407.
Zhang, W. et al., "Multiple Components of the Defense Response Depend on Orexin: Evidence from Orexin Knockout Mice and Orexin Neuron-Ablated Mice," Autonomic Neuroscience: Basic and Clinical, 2006, 126-127, 139-145.

PROLINE SULFONAMIDE DERIVATIVES AS OREXIN RECEPTOR ANTAGONISTS

CROSS REFERENCE TO RELATED APPLICATIONS

This application is a continuation of U.S. patent application Ser. No. 13/818,647, filed on Feb. 22, 2013, which is a U.S. National Phase Application under 35 U.S.C. §371 of International Application No. PCT/IB2011/053693, filed on Aug. 23, 2011, which claims priority of International Application No. PCT/IB2010/053799, filed on Aug. 24, 2010, the contents of each of which are hereby incorporated by reference in their entirety.

The present invention relates to (S)-proline sulfonamide compounds of formula (I), or pharmaceutically acceptable salts thereof, and to pharmaceutical compositions comprising such compounds, for the prevention or treatment of diseases or disorders related to the orexin system. The present invention especially relates to the use of (S)-proline sulfonamide compounds of formula (II) as medicaments, to pharmaceutical compositions containing one or more compounds of formula (II), and to the use of such compound or pharmaceutical composition for the prevention or treatment of diseases or disorders related to the orexin system, especially for the prevention or treatment of sleep disorders, anxiety disorders, addiction disorders, cognitive dysfunctions, mood disorders, or appetite disorders. The invention also concerns related aspects including processes for the preparation of said compounds.

Orexins (orexin A or OX-A and orexin B or OX-B) are novel neuropeptides found in 1998 by two research groups, orexin A is a 33 amino acid peptide and orexin B is a 28 amino acid peptide [Sakurai T. et al., Cell, 1998, 92, 573-585]. Orexins are produced in discrete neurons of the lateral hypothalamus and bind to the G-protein-coupled receptors ($OX_1$ and $OX_2$ receptors). The orexin-1 receptor ($OX_1$) is selective for OX-A, and the orexin-2 receptor ($OX_2$) is capable to bind OX-A as well as OX-B. Orexins have initially been found to stimulate food consumption in rats suggesting a physiological role for these peptides as mediators in the central feedback mechanism that regulates feeding behaviour [Sakurai T. et al., Cell, 1998, 92, 573-585].

On the other hand, orexin neuropeptides and orexin receptors play an essential and central role in regulating circadian vigilance states. In the brain, orexin neurons collect sensory input about internal and external states and send short intrahypothalamic axonal projections as well as long projections to many other brain regions. The particular distribution of orexin fibers and receptors in basal forebrain, limbic structures and brainstem regions—areas related to the regulation of waking, sleep and emotional reactivity—suggests that orexins exert essential functions as regulators of behavioral arousal; by activating wake-promoting cell firing, orexins contribute to orchestrate all brain arousal systems that regulate circadian activity, energy balance and emotional reactivity. This role opens large therapeutic opportunities for medically addressing numerous mental health disorders possibly relating to orexinergic dysfunctions [see for example: Tsujino N and Sakurai T, "Orexin/hypocretin: a neuropeptide at the interface of sleep, energy homeostasis, and reward systems.", Pharmacol Rev. 2009, 61:162-176; and Carter M E et al., "The brain hypocretins and their receptors: mediators of allostatic arousal.", Curr Op Pharmacol. 2009, 9: 39-45] that are described in the following sections.

It was observed that orexins regulate states of sleep and wakefulness (Chemelli R. M. et al., Cell 1999, 98, 437-451). Infusing orexins intracerebrally in rats leads to enhanced behavioral activity, arousal, delayed onset of REM, and maintenance of cortical activation [Kiwaki K et al., Am J Physiol Endocrinol Metab 2004, 286(4), E551-559; Piper D C et al., Eur J Neurosci 2000, 12(2), 726-730; Samson W K et al., Acta Physiol (Oxf) 2010, 198(3), 313-324]. Orexin-producing neurons are active during wakefulness and fall quiet during sleep [see for example Lee M G et al., J Neurosci 2005, 25(28), 6716-6720; Mileykovskiy B Y et al., Neuron 2005, 46(5), 787-798]. Orexin-A levels in the cerebrospinal fluid of several species fluctuate according to circadian rhythms; they are highest during active wake periods [Desarnaud F et al., Sleep 2004, 27(5), 851-856; Kiyashchenko L I et al., J Neurosci 2002, 22(13), 5282-5286; Salomon R M et al., Biol Psychiatry 2003, 54(2), 96-104; Zeitzer J M et al., J Neurosci 2003, 23(8), 3555-3560].

The compound (2R)-2-{(1S)-6,7-dimethoxy-1-[2-(4-trifluoromethyl-phenyl)-ethyl]-3,4-dihydro-1H-isoquinolin-2-yl}-N-methyl-2-phenyl-acetamide (WO2005/118548), a dual orexin receptor antagonist, showed clinical efficacy in humans when tested for the indication primary insomnia. In the rat, the compound has been shown to decrease alertness, characterized by decreases in both active wake and locomotion; and to dose-dependently increase the time spent in both REM and NREM sleep [Brisbare et al., Nature Medicine 2007, 13, 150-155].

In addition, both anatomical and functional evidence from in vitro and in vivo studies suggest an important positive interaction of the endogenous orexin system with reward pathways of the brain [Aston-Jones G et al., "Stress, eating and the reward system." Brain Res 2010, 1314, 74-90; Sharf R et al., "Role of orexin/hypocretin in dependence and addiction." Brain Res 2010, 1314, 130-138]. Orexin neurons become activated upon exposure to reward-related contextual cues [Harris G C et al., "A role for lateral hypothalamic orexin neurons in reward seeking." Nature 2005, 437(7058), 556-559] and chronic administration of drugs of abuse leads to long-term changes in orexin and/or OXR expression [Kane J K et al., "Nicotine up-regulates expression of orexin and its receptors in rat brain." Endocrinology 2000, 141(10), 3623-3629; Zhang G C, et al., "Long-lasting up-regulation of orexin receptor type 2 protein levels in the rat nucleus accumbens after chronic cocaine administration." J Neurochem 2007, 103(1), 400-407]. Furthermore, orexin deficient mice showed reduced conditioned place preference to morphine and showed less severe morphine withdrawal signs [Georgescu D et al., J Neurosci 2003, 23(8), 3106-3111; Narita M et al., J Neurosci 2006, 26(2): 398-405]. Selective pharmacological OXR-1 blockade reduced cue- and stress-induced reinstatement of cocaine seeking [Boutrel B, et al., "Role for hypocretin in mediating stress-induced reinstatement of cocaine-seeking behavior." Proc Natl Acad Sci 2005, 102(52), 19168-19173; Smith R J et al., "Orexin/hypocretin signaling at the orexin 1 receptor regulates cue-elicited cocaine-seeking." Eur J Neurosci 2009, 30(3), 493-503; Smith R J et al., "Orexin/hypocretin is necessary for context-driven cocaine-seeking." Neuropharmacology 2010, 58(1), 179-184], cue-induced reinstatement of alcohol seeking [Lawrence A J et al., Br J Pharmacol 2006, 148(6), 752-759] and nicotine self-administration [Hollander J A et al., Proc Natl Acad Sci 2008, 105(49), 19480-19485; LeSage M G et al., Psychopharmacology 2010, 209(2), 203-212]. OXR-1 antagonism also attenuated the expression of amphetamine- and cocaine-induced CPP [Gozzi A et al., PLoS One 2011, 6(1), e16406; Hutcheson D M et al., Behav Pharmacol 2011, 22(2), 173-181], and reduced the expression or development of locomotor sensitization to amphetamine and cocaine [Borgland S L et al., "Orexin A in the VTA is critical for the induction of synaptic plasticity and behavioral sensitization to cocaine." Neuron 2006, 49(4), 589-601; Quarta D et al., "The orexin-1 receptor antagonist SB-334867 reduces amphetamine-evoked dopamine outflow in the shell of the nucleus accumbens and decreases the expression of amphetamine sensitization." Neurochem Int 2010, 56(1), 11-15].

The effect of a drug to diminish addictions may be modelled in normal or particularly sensitive mammals used as animal models [see for example Spealman et al, Pharmacol. Biochem. Behav. 1999, 64, 327-336; or T. S. Shippenberg, G. F. Koob, "Recent advances in animal models of drug addiction" in Neuropsychopharmacology: The fifth generation of progress; K. L. Davis, D. Charney, J. T. Doyle, C. Nemeroff (eds.) 2002; chapter 97, pages 1381-1397]. The compound (2R)-2-{(1S)-6,7-dimethoxy-1-[2-(4-trifluoromethyl-phenyl)-ethyl]-3,4-dihydro-1H-isoquinolin-2-yl}-N-methyl-2-phenyl-acetamide (WO2005/118548), a dual orexin receptor antagonist, displayed pharmacological activity in a rat model of nicotine self-administration [LeSage M G et al., "Nicotine self-administration in the rat: effects of hypocretin antagonists and changes in hypocretin mRNA." Psychopharmacology 2010, 209(2), 203-212]. Another dual orexin receptor antagonist, N-biphenyl-2-yl-1-{[(1-methyl-1Hbenzimidazol-2-yl)sulfanyl]acetyl}-L-prolinamide inhibited nicotine-reinstatement for a conditioned reinforcer and reduced behavioral (locomotor sensitization) and molecular (transcriptional responses) changes induced by repeated amphetamine administration in rodents [Winrow et al., Neuropharmacology 2009, 58(1), 185-94].

Several converging lines of evidence demonstrate a direct role of the orexin system as modulator of the acute stress response. For instance, stress (i.e. psychological stress or physical stress) is associated with increased arousal and vigilance which in turn is controlled by orexins [Sutcliffe, J G et al., "The hypocretins: setting the arousal threshold." Nat Rev Neurosci 2002, 3(5), 339-349]. Orexin neurons are likely to be involved in the coordinated regulation of behavioral and physiological responses in stressful environments [Y. Kayaba et al., Am. J. Physiol. Regul. Integr. Comp. Physiol. 2003, 285:R581-593]. Hypocretin/orexin contributes to the expression of some but not all forms of stress and arousal [Furlong T M et al., "Hypocretin/orexin contributes to the expression of some but not all forms of stress and arousal." Eur J Neurosci 2009, 30(8), 1603-1614]. Stress response may lead to dramatic, usually time-limited physiological, psychological and behavioural changes that may affect appetite, metabolism and feeding behavior [Chrousos, G P et al., *JAMA* 1992, 267(9), 1244-1252]. The acute stress response may include behavioural, autonomic and endocrinological changes, such as promoting heightened vigilance, decreased libido, increased heart rate and blood pressure, or a redirection of blood flow to fuel the muscles, heart and the brain [Majzoub, J A et al., European Journal of Endocrinology 2006, 155 (suppl_1) S71-S76].

The compound (2R)-2-{(1S)-6,7-dimethoxy-1-[2-(4-trifluoromethyl-phenyl)-ethyl]-3,4-dihydro-1H-isoquinolin-2-yl}-N-methyl-2-phenyl-acetamide (WO2005/118548), a dual orexin receptor antagonist, attenuated cardiovascular responses to conditioned fear and novelty exposure in rats [Furlong T M et al., Eur J Neurosci 2009, 30(8), 1603-1614]. It is also active in an animal model of conditioned fear: the rat fear-potentiated startle paradigm (WO2009/0047723) which relates to emotional states of fear and anxiety diseases such as anxieties including phobias and post traumatic stress disorders (PTSDs).

The orexin system is also involved in stress-related appetitive/reward seeking behaviour (Berridge C W et al., "Hypocretin/orexin in arousal and stress." Brain Res 2009, 1314, 91-102). In certain instances, a modulatory effect on stress may be complementary to an effect on appetitive/reward seeking behaviour as such. For instance, an $OX_1$ selective orexin receptor antagonist was able to prevent footshock stress induced reinstatement of cocaine seeking behaviour [Boutrel, B et al., "Role for hypocretin in mediating stress-induced reinstatement of cocaine-seeking behavior." Proc Natl Acad Sci 2005, 102(52), 19168-19173]. In addition, stress is also known to play an integral part in withdrawal which occurs during cessation of drug taking (Koob, G F et al., Curr Opin Investig Drugs 2010, 11(1), 63-71).

Human memory is comprised of multiple systems that have different operating principles and different underlying neuronal substrates. The major distinction is between the capacity for conscious, declarative memory and a set of unconscious, non-declarative memory abilities. Declarative memory is further subdivided into semantic and episodic memory. Non-declarative memory is further subdivided into priming and perceptual learning, procedural memory for skills and habits, associative and non-associative learning, and some others. While semantic memory refers to the general knowledge about the world, episodic memory is autobiographical memory of events. Procedural memories refer to the ability to perform skill-based operations, as e.g. motor skills. Long-term memory is established during a multiple stage process through gradual changes involving diverse brain structures, beginning with learning, or memory acquisition, or formation. Subsequently, consolidation of what has been learned may stabilize memories. When long-term memories are retrieved, they may return to a labile state in which original content may be updated, modulated or disrupted. Subsequently, reconsolidation may again stabilize memories. At a late stage, long-term memory may be resistant to disruption. Long-term memory is conceptually and anatomically different from working memory, the latter of which is the capacity to maintain temporarily a limited amount of information in mind. Behavioural research has suggested that the human brain consolidates long-term memory at certain key time intervals. The initial phase of memory consolidation may occur in the first few minutes after we are exposed to a new idea or learning experience. The next, and possibly most important phase, may occur over a longer period of time, such as during sleep; in fact, certain consolidation processes have been suggested to be sleep-dependent [R. Stickgold et al., Sleep-dependent memory consolidation; Nature 2005, 437, 1272-1278]. Learning and memory processes are believed to be fundamentally affected in a variety of neurological and mental disorders, such as e.g. mental retardation, Alzheimer's disease or depression. Indeed, memory loss or impairment of memory acquisition is a significant feature of such diseases, and no effective therapy to prevent this detrimental process has emerged yet.

Intact declarative and non-declarative learning and memory has been demonstrated in rats treated with the compound (2R)-2-{(1S)-6,7-dimethoxy-1-[2-(4-trifluoromethyl-phenyl)-ethyl]-3,4-dihydro-1H-isoquinolin-2-yl}-N-methyl-2-phenyl-acetamide (WO2005/118548, WO2007/105177), a dual orexin receptor antagonist [H Dietrich, F Jenck, Psychopharmacology 2010, 212, 145-154]. The said compound furthermore decreased brain levels of amyloid-beta (Aβ) as well as Aβ plaque deposition after acute sleep restriction in amyloid precursor protein transgenic mice [J E Kang et al., "Amyloid-beta dynamics are regulated by orexin and the sleep-wake cycle.", Science 2009, 326(5955): 1005-

1007]. The accumulation of the Aβ in the brain extracellular space is hypothesized to be a critical event in the pathogenesis of Alzheimer's disease. The so-called and generally known "amyloid cascade hypothesis" links Aβ to Alzheimer's disease and, thus, to the cognitive dysfunction, expressed as impairment of learning and memory.

As outlined above the orexin system regulates homeostatic functions such as sleep-wake cycle, energy balance, emotions and reward [Tsujino N, Sakurai T "Orexin/Hypocretin: a neuropeptide at the interface of sleep, energy homeostasis, and reward system." Pharmacol Rev 2009, 61(2) 162-176]. Orexins are also involved in mediating the acute behavioral and autonomous nervous system response to stress [Zhang W et al., "Multiple components of the defense response depend on orexin: evidence from orexin knockout mice and orexin neuron-ablated mice." Auton Neurosci 2006, 126-127, 139-145]. Mood disorders including all types of depression and bipolar disorder are characterized by disturbed "mood" and feelings, as well as by sleeping problems (insomnia as well as hypersomnia), changes in appetite or weight and reduced pleasure and loss of interest in daily or once enjoyed activities [Liu X et al., "Insomnia and hypersomnia associated with depressive phenomenology and comorbidity in childhood depression." Sleep 2007, 30(1): 83-90]. Thus, there is a strong rationale that disturbances in the orexin system may contribute to the symptoms of mood disorders. Evidence in humans, for instance, exists that depressed patients show blunted diurnal variation in CSF orexin levels [Salomon R M et al., Biol Psychiatry 2003, 54(2), 96-104]. In rodent models of depression, orexins were also shown to be involved. Pharmacological induction of a depressive behavioral state in rats, for instance, revealed an association with increased hypothalamic orexin levels [Feng P et al., "Changes in brain orexin levels in a rat model of depression induced by neonatal administration of clomipramine." J Psychopharmacol 2008, 22(7): 784-791]. A chronic stress model of depression in mice also demonstrated an association of molecular orexin system disturbances with depressed behavioral states and a reversal of these molecular changes by antidepressant treatment [Nollet et al., "Activation of orexin neurons in dorsomedial/perifornical hypothalamus and antidepressant reversal in a rodent model of depression." NeuroPharm 2011, 61(1-2):336-46].

The compound (2R)-2-{(1S)-6,7-dimethoxy-1-[2-(4-trifluoromethyl-phenyl)-ethyl]-3,4-dihydro-1H-isoquinolin-2-yl}-N-methyl-2-phenyl-acetamide (WO2005/118548), a dual orexin receptor antagonist, has been shown to induce antidepressant-like activity in a mouse model of depression, when administered chronically [Nollet et al., NeuroPharm 2011, 61(1-2):336-46].

Orexins have been found to increase food intake and appetite [Tsujino, N, Sakurai, T, "Orexin/Hypocretin: a neuropeptide at the interface of sleep, energy homeostasis, and reward system." Pharmacol Rev 2009, 61(2) 162-176]. As an additional environmental factor, stress can contribute to binge eating behaviour, and lead to obesity [Adam, T C et al. "Stress, eating and the reward system." Physiol Behav 2007, 91(4) 449-458]. Animal models that are clinically relevant models of binge eating in humans are described for example in W. Foulds Mathes et al., "The biology of binge eating"; Appetite 2009, 52, 545-553.

The compound (2R)-2-{(1S)-6,7-dimethoxy-1-[2-(4-trifluoromethyl-phenyl)-ethyl]-3,4-dihydro-1H-isoquinolin-2-yl}-N-methyl-2-phenyl-acetamide (WO2005/118548), a dual orexin receptor antagonist, has been shown to attenuate the natural activation induced by orexin A in fasted hungry rats exposed to food odors [M J Prud'homme et al., "Nutritional status modulates behavioural and olfactory bulb Fos responses to isoamyl acetate or food odour in rats: roles of orexins and leptin." Neuroscience 2009, 162(4), 1287-1298].

A number of recent studies report that orexins may play a role into several other important functions relating to arousal, especially when an organism must respond to unexpected stressors and challenges in the environment [Tsujino N and Sakurai T. Pharmacol Rev. 2009, 61:162-176; Carter M E, Borg J S and deLecea L. The brain hypocretins and their receptors: mediators of allostatic arousal, Curr Op Pharmacol. 2009, 9: 39-45; C Boss, C Brisbare-Roch, F Jenck, Biomedical Applications of Orexin/Hypocretin Receptor Ligands in Neuroscience, Journal of Medicinal Chemistry 2009, 52: 891-903]. The orexin system interacts with neural networks that regulate emotion, reward and energy homeostasis to maintain proper vigilance states. Dysfunctions in its function may thus relate to many mental health disorders in which vigilance, arousal, wakefulness or attention is disturbed.

Certain pyrrolidine sulfonamide orexin receptor antagonists are known from WO2004/041807, however, these compounds do not carry the amide moiety of the present proline sulfonamide derivatives. Certain proline sulfonamide derivatives are known from the chemical abstracts databases in racemic form or in the particular (S)-configuration. However, no use of these compounds is disclosed in the prior art. In addition, WO2006/022442 discloses compounds that are dihydoorotate dehydrogenase (DHODH) inhibitors, encompassing the (R)-configured compound (R)-1-(4-chlorobenzenesulfonyl)-pyrrolidine-2-carboxylic acid-(4-chloro-phenyl)-amide. Furthermore, the particular compounds: (S)-1-(4-methylbenzene sulfonyl)-pyrrolidine-2-carboxylic acid-(3,4-dichloro-phenyl)-amide (CAS Registry 77007-21-7); (S)-1-(4-methylbenzene-sulfonyl)-pyrrolidine-2-carboxylic acid phenyl-amide (CAS Registry 73096-29-4); and (S)-1-(4-methylbenzenesulfonyl)-pyrrolidine-2-carboxylic acid (4-methyl-phenyl)-amide (CAS Registry 73096-28-3); are known as quality improvers for citrus fruits ["Plant regulating compositions for modifying the acid content of citrus fruits."; Tsuruta, Terayuki et. al., U.S. Pat. No. 4,217,130; "Pyrrolidine derivatives"; JP 55081857 (1980); (Kyowa Hakko Kogyo Co., Ltd., Japan)].

The present invention provides proline sulfonamide compounds, which, when in the particular (S)-configuration, have surprisingly been found to act as potent non-peptide antagonists of human orexin receptors and, thus, are of potential use in the treatment of diseases or disorders related to the orexin system, comprising especially sleep disorders, anxiety disorders, addiction disorders, cognitive dysfunctions, mood disorders, or appetite disorders.

For comparison, the compound (R)-1-(4-methoxy-benzenesulfonyl)-pyrrolidine-2-carboxylic acid (3,5-dimethyl-phenyl)-amide has been tested for its pharmacological activity and it was found to inhibit the human orexin receptors significantly less than the (S)-configured compounds of the present invention.

SHORT DESCRIPTION OF THE FIGURES

DETAILED DESCRIPTION OF THE INVENTION

Figure 1:
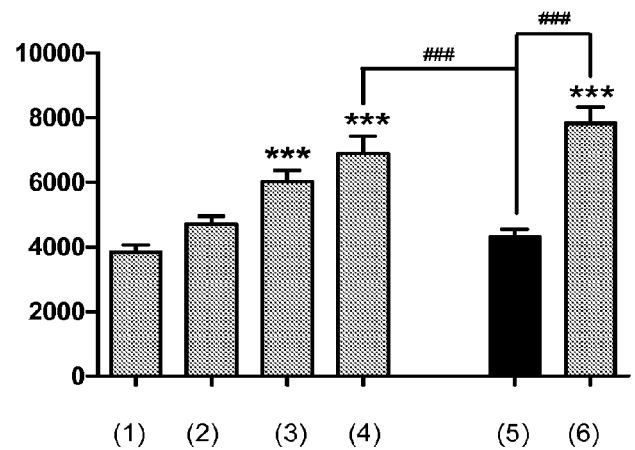
FIG. 1 shows the effects of the compound of example 26 on morphine-induced locomotor sensitization.

1) A first aspect of the invention relates to proline sulfonamide compounds, or pharmaceutically acceptable salts thereof, for the prevention or treatment of diseases or disorders related to the orexin system; wherein said compounds are compounds of the formula (I)

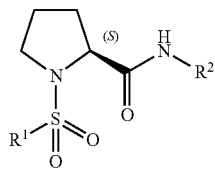

Formula (I)

wherein
the absolute configuration at the center of chirality is (S);
$R^1$ represents aryl or thienyl; wherein the aryl or thienyl is independently mono-, di-, or tri-substituted; wherein the substituents are independently selected from the group consisting of $(C_{1-4})$alkyl, $(C_{1-4})$alkoxy, cyano, halogen, $(C_{1-3})$fluoroalkyl, $(C_{1-3})$fluoroalkoxy, methanesulfonyl, and vinyl;
wherein, in case $R^1$ represents a naphthyl group, such naphthyl group may additionally be unsubstituted;
or $R^1$ represents a 4-methyl-3,4-dihydro-2H-benzo[1,4]oxazinyl group; and
$R^2$ represents aryl, wherein the aryl is unsubstituted, or mono-, di-, or tri-substituted, wherein the substituents are independently selected from the group consisting of $(C_{1-4})$alkyl, $(C_{1-4})$alkoxy, cyano, halogen, $(C_{1-3})$fluoroalkyl, $(C_{1-3})$fluoroalkoxy, dimethylamino, cyano, and $(C_{1-3})$alkyl-thio-; or $R^2$ represents an indanyl group.

For avoidance of any doubt, if compounds are described for the prevention or treatment of certain diseases or disorders, such compounds are likewise suitable for use in the preparation of a medicament for the prevention or treatment of said diseases or disorders.

In this patent application, a bond depicted as a dotted line indicates the point of attachment of the radical drawn. For example, the radical drawn below

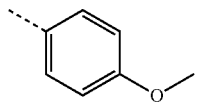

is the 4-methoxy-phenyl group.

Where the plural form is used for compounds, salts, pharmaceutical compositions, diseases or the like, this is intended to mean also a single compound, salt, disease or the like.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

The term "halogen" means fluorine, chlorine, or bromine. For the substituents of the group $R^1$ representing an aryl or thienyl group the term notably refers to chlorine or bromine.

The term "alkyl", used alone or in combination, refers to a saturated straight or branched chain alkyl group containing one to four carbon atoms. The term "$(C_{x-y})$alkyl" (x and y each being an integer), refers to an alkyl group as defined before containing x to y carbon atoms. For example a $(C_{1-4})$ alkyl group contains from one to four carbon atoms. Examples of $(C_{1-4})$alkyl groups are methyl, ethyl, propyl, isopropyl, n-butyl, isobutyl, and sec.-butyl. Preferred are methyl and ethyl. Most preferred is methyl. For the substituents of the group $R^1$ representing an aryl group, the term notably refers to $(C_{1-3})$alkyl, especially to methyl. For the substituents of the group $R^2$ representing an aryl group, the term notably refers to $(C_{1-3})$alkyl, especially to methyl or ethyl.

The term "alkoxy", used alone or in combination, refers to an alkyl-O— group wherein the alkyl group is as defined before. The term "$(C_{x-y})$alkoxy" (x and y each being an integer) refers to an alkoxy group as defined before containing x to y carbon atoms. For example a $(C_{1-4})$alkoxy group means a group of the formula $(C_{1-4})$alkyl-O— in which the term "$(C_{1-4})$alkyl" has the previously given significance. Examples of $(C_{1-4})$alkoxy groups are methoxy, ethoxy, n-propoxy, isopropoxy, n-butoxy, isobutoxy, sec.-butoxy and tert.-butoxy. Preferred are ethoxy and especially methoxy.

The term "fluoroalkyl" refers to an alkyl group as defined before containing one to three carbon atoms in which one or more (and possibly all) hydrogen atoms have been replaced with fluorine. The term "$(C_{x-y})$fluoroalkyl" (x and y each being an integer) refers to a fluoroalkyl group as defined before containing x to y carbon atoms. For example a $(C_{1-3})$ fluoroalkyl group contains from one to three carbon atoms in which one to seven hydrogen atoms have been replaced with fluorine. Representative examples of fluoroalkyl groups include trifluoromethyl and 2,2,2-trifluoroethyl. Preferred are $(C_1)$fluoroalkyl groups such as trifluoromethyl.

The term "fluoroalkoxy" refers to an alkoxy group as defined before containing one to three carbon atoms in which one or more (and possibly all) hydrogen atoms have been replaced with fluorine. The term "$(C_{x-y})$fluoroalkoxy" (x and y each being an integer) refers to a fluoroalkoxy group as defined before containing x to y carbon atoms. For example a $(C_{1-3})$fluoroalkoxy group contains from one to three carbon atoms in which one to seven hydrogen atoms have been replaced with fluorine. Representative examples of fluoroalkoxy groups include trifluoromethoxy, difluoromethoxy and 2,2,2-trifluoroethoxy. Preferred are $(C_1)$fluoroalkoxy groups such as trifluoromethoxy and difluoromethoxy.

The term "aryl", alone or in combination, means a phenyl or a naphthyl group. Preferred is phenyl. The aryl group may be unsubstituted or substituted as explicitly defined.

For the substituent $R^1$ the term notably means phenyl which may be substituted as explicitly defined. Particular examples of aryl groups as used for the substituent $R^1$ are 5-bromo-thiophen-2-yl, 4-chloro-phenyl, 3-chloro-phenyl, 4-bromo-phenyl, 3-bromo-phenyl, 3-chloro-4-methyl-phenyl, 2-bromo-4-methyl-phenyl, 4-bromo-2-methyl-phenyl, 4-vinyl-phenyl, 2,4-dimethylphenyl, 3,4-dichloro-phenyl, 4-bromo-2-chloro-phenyl, 3-methoxy-phenyl, 4-methoxy-phenyl, 4-chloro-2,5-dimethyl-phenyl, 4-n-propyl-phenyl, 2-methoxy-4-methyl-phenyl, 2-methoxy-5-methyl-phenyl, 4-trifluoromethyl-phenyl, 4-methanesulfonyl-phenyl, 2,5-dimethoxy-phenyl, 3,4-dimethoxy-phenyl, naphthalen-1-yl, naphthalen-2-yl, 2-chloro-5-trifluoromethyl-phenyl, 2-chloro-4-trifluoromethyl-phenyl, and 4-chloro-3-trifluoromethyl-phenyl.

For the substituent $R^2$ the term notably means phenyl which may be unsubstituted or substituted as explicitly defined. Particular examples of aryl groups as used for the substituent $R^2$ are phenyl, 3-chloro-phenyl, 3-bromo-phenyl, 3-methyl-phenyl, 3-methylthio-phenyl, 2-chloro-5-methyl-phenyl, 4-chloro-3-methyl-phenyl, 2-fluoro-5-methyl-phenyl, 4-fluoro-3-methyl-phenyl, 3-ethyl-phenyl, 3,5-dimethylphenyl, 3,4-dimethyl-phenyl, 3,4-dichloro-phenyl, 3,5-dichloro-phenyl, 3-chloro-4-fluoro-phenyl, 3,4-difluoro-phenyl, 3-methoxy-phenyl, 3-cyano-phenyl, 5-chloro-2-methoxy-phenyl, 2-chloro-5-methoxy-phenyl, 3-ethoxy-phenyl, 3-dimethylamino-phenyl, 3-trifluoromethyl-phenyl, 3,5-dimethoxy-phenyl, 1-naphthyl, 3-trifluoromethoxy-phenyl, and 3,5-bistrifluoromethyl-phenyl.

Thienyl (or thiophenyl) groups as used for the substituent $R^1$ are especially 2-thienyl(thiophen-2-yl) groups. Preferred examples of $R^1$ representing a thienyl group, wherein the thienyl is mono-, di-, or tri-substituted, wherein the substituents are independently selected from the group consisting of $(C_{1-4})$alkyl, $(C_{1-4})$alkoxy, halogen, $(C_{1-3})$fluoroalkyl, $(C_{1-3})$fluoroalkoxy, methanesulfonyl, and vinyl are those groups wherein the thienyl is mono- or di-substituted (notably mono-substituted); and especially those groups wherein the substituents are independently selected from the group consisting of $(C_{1-4})$alkyl, and halogen; especially the substituents are halogen, notably bromo. A particular example is 5-bromo-thiophen-2-yl.

The term "$(C_{x-y})$alkyl-thio" refers to an alkyl group containing x to y carbon atoms as defined before, said group being attached to the rest of the molecule via a sulfur atom. For example a $(C_{1-3})$alkyl-thio group contains from one to three carbon atoms. A representative example of a $(C_{1-3})$alkyl-thio group is methyl-sulfanyl (methylthio, $H_3C$—S—).

An example for an indanyl group is indan-5-yl. An example of an 4-methyl-3,4-dihydro-2H-benzo[1,4]oxazinyl group is 4-methyl-3,4-dihydro-2H-benzo[1,4]oxazin-7-yl.

Further embodiments of the invention are presented hereafter:

2) A further embodiment of the invention relates to compounds according to embodiment 1), or pharmaceutically acceptable salts thereof, for the prevention or treatment of diseases or disorders related to the orexin system; wherein $R^1$ represents a group selected from the group consisting of:

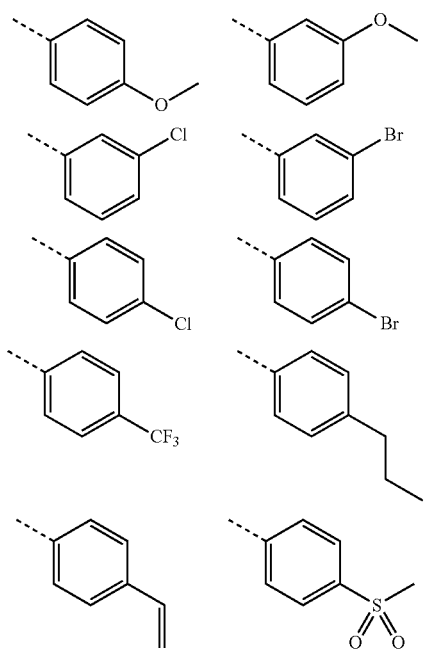

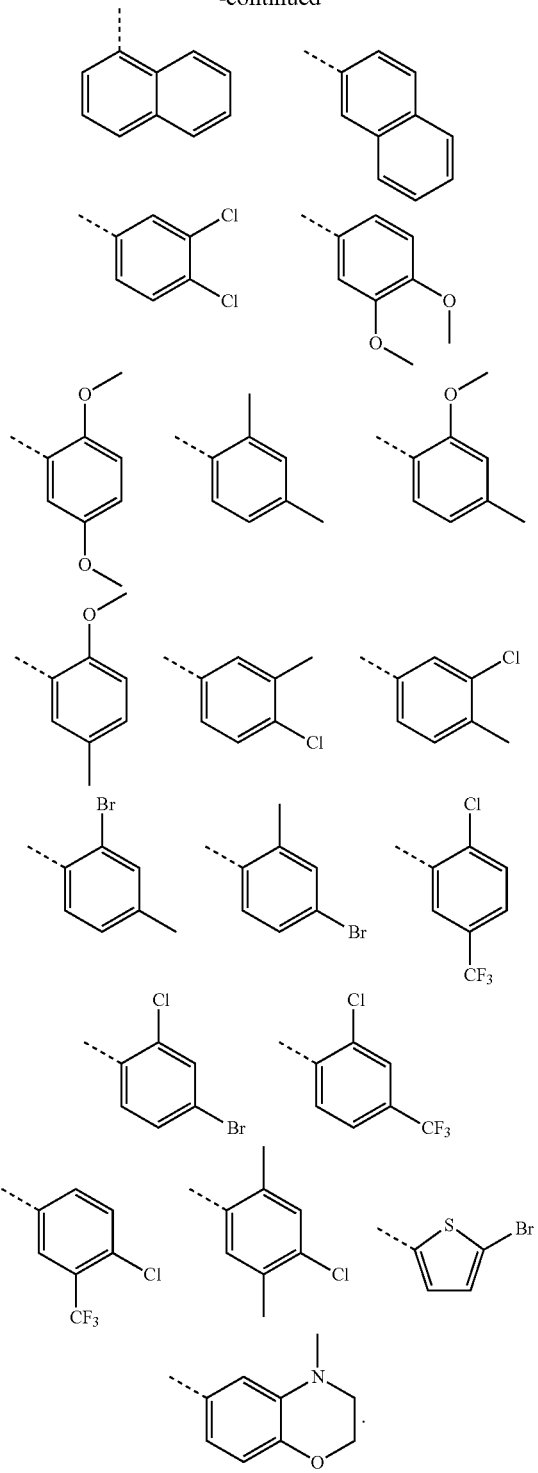

3) A further embodiment of the invention relates to compounds according to embodiment 1), or pharmaceutically acceptable salts thereof, for the prevention or treatment of diseases or disorders related to the orexin system; wherein $R^1$ represents aryl which is mono-, di-, or tri-substituted, wherein the substituents are independently selected from the group consisting of $(C_{1-4})$alkyl, $(C_{1-4})$alkoxy, halogen, $(C_{1-3})$fluoroalkyl, and $(C_{1-3})$fluoroalkoxy (especially $(C_{1-4})$alkyl, $(C_{1-4})$alkoxy, halogen, and $(C_{1-3})$fluoroalkyl).

4) A further embodiment of the invention relates to compounds according to embodiment 1), or pharmaceutically acceptable salts thereof, for the prevention or treatment of diseases or disorders related to the orexin system; wherein $R^1$ represents aryl which is mono-, or di-substituted, wherein the substituents are independently selected from the group consisting of $(C_{1-4})$alkyl, $(C_{1-4})$alkoxy, halogen, and $(C_{1-3})$fluoroalkyl.

5) A further embodiment of the invention relates to compounds according to embodiment 1), or pharmaceutically acceptable salts thereof, for the prevention or treatment of diseases or disorders related to the orexin system; wherein $R^1$ represents a group selected from the group consisting of 5-bromo-thiophen-2-yl, 4-chloro-phenyl, 3-chloro-phenyl, 4-bromo-phenyl, 3-bromo-phenyl, 3-chloro-4-methyl-phenyl, 2-bromo-4-methyl-phenyl, 4-bromo-2-methyl-phenyl, 4-vinyl-phenyl, 2,4-dimethylphenyl, 3,4-dichloro-phenyl, 4-bromo-2-chloro-phenyl, 3-methoxy-phenyl, 4-methoxy-phenyl, 4-chloro-2,5-dimethyl-phenyl, 4-n-propyl-phenyl, 2-methoxy-4-methyl-phenyl, 2-methoxy-5-methyl-phenyl, 4-trifluoromethyl-phenyl, 4-methanesulfonyl-phenyl, 2,5-dimethoxy-phenyl, 3,4-dimethoxy-phenyl, naphthalen-1-yl, naphthalen-2-yl, 4-methyl-3,4-dihydro-2H-benzo[1,4]oxazin-7-yl, 2-chloro-5-trifluoromethyl-phenyl, 2-chloro-4-trifluoromethyl-phenyl, and 4-chloro-3-trifluoromethyl-phenyl.

6) A further embodiment of the invention relates to compounds according to embodiment 1), or pharmaceutically acceptable salts thereof, for the prevention or treatment of diseases or disorders related to the orexin system; wherein $R^1$ represents a group selected from the group consisting of:

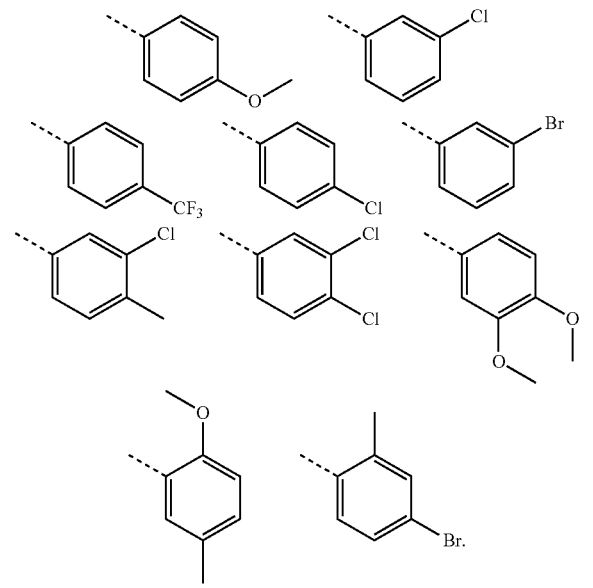

7) A further embodiment of the invention relates to compounds according to embodiment 1), or pharmaceutically acceptable salts thereof, for the prevention or treatment of diseases or disorders related to the orexin system; wherein $R^1$ represents a group selected from the group consisting of 4-chloro-phenyl, 3-chloro-phenyl, 4-bromo-phenyl, 3-bromo-phenyl, 3-chloro-4-methyl-phenyl, 3,4-dichloro-phenyl, 3-methoxy-phenyl, 4-methoxy-phenyl, 2-methoxy-5-methyl-phenyl, 4-trifluoromethyl-phenyl, 3,4-dimethoxy-phenyl, 2-chloro-4-trifluoromethyl-phenyl, and 4-chloro-3-trifluoromethyl-phenyl.

8) A further embodiment of the invention relates to compounds according to embodiment 1), or pharmaceutically acceptable salts thereof, for the prevention or treatment of diseases or disorders related to the orexin system; wherein $R^1$ represents a group selected from the group consisting of 4-chloro-phenyl, 3-chloro-phenyl, 4-bromo-phenyl, 3-bromo-phenyl, 3-chloro-4-methyl-phenyl, 3,4-dichloro-phenyl, 3-methoxy-phenyl, 4-methoxy-phenyl, and 3,4-dimethoxy-phenyl.

9) A further embodiment of the invention relates to compounds according to embodiment 1), or pharmaceutically acceptable salts thereof, for the prevention or treatment of diseases or disorders related to the orexin system; wherein $R^1$ represents a group selected from the group consisting of 4-chloro-phenyl, 3-chloro-phenyl, 4-bromo-phenyl, 3-bromo-phenyl, 3-chloro-4-methyl-phenyl, and 3,4-dichloro-phenyl.

10) A further embodiment of the invention relates to compounds according to embodiment 1), or pharmaceutically acceptable salts thereof, for the prevention or treatment of diseases or disorders related to the orexin system; wherein $R^1$ represents a group selected from the group consisting of 3-methoxy-phenyl, 4-methoxy-phenyl, and 3,4-dimethoxy-phenyl.

11) A further embodiment of the invention relates to compounds according to embodiment 1), or pharmaceutically acceptable salts thereof, for the prevention or treatment of diseases or disorders related to the orexin system; wherein $R^1$ represents a group selected from the group consisting of:

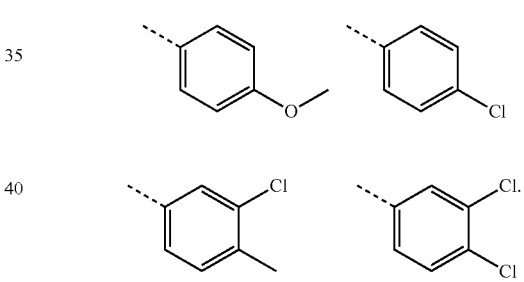

12) A further embodiment of the invention relates to compounds according to any one of embodiments 1) to 11), or pharmaceutically acceptable salts thereof, for the prevention or treatment of diseases or disorders related to the orexin system; wherein, in case $R^1$ represents phenyl, such phenyl is substituted as explicitly defined, wherein at least one substituent is attached in position 4 of the phenyl ring (it being well understood that position 4 designates the para-position with regard to the point of attachment of the rest of the molecule to said phenyl ring).

13) A further embodiment of the invention relates to compounds according to embodiment 1), or pharmaceutically acceptable salts thereof, for the prevention or treatment of diseases or disorders related to the orexin system; wherein $R^1$ represents 4-methoxy-phenyl.

14) A further embodiment of the invention relates to compounds according to any one of embodiments 1) to 13), or pharmaceutically acceptable salts thereof, for the prevention or treatment of diseases or disorders related to the orexin system; wherein $R^2$ represents a group selected from the group consisting of:

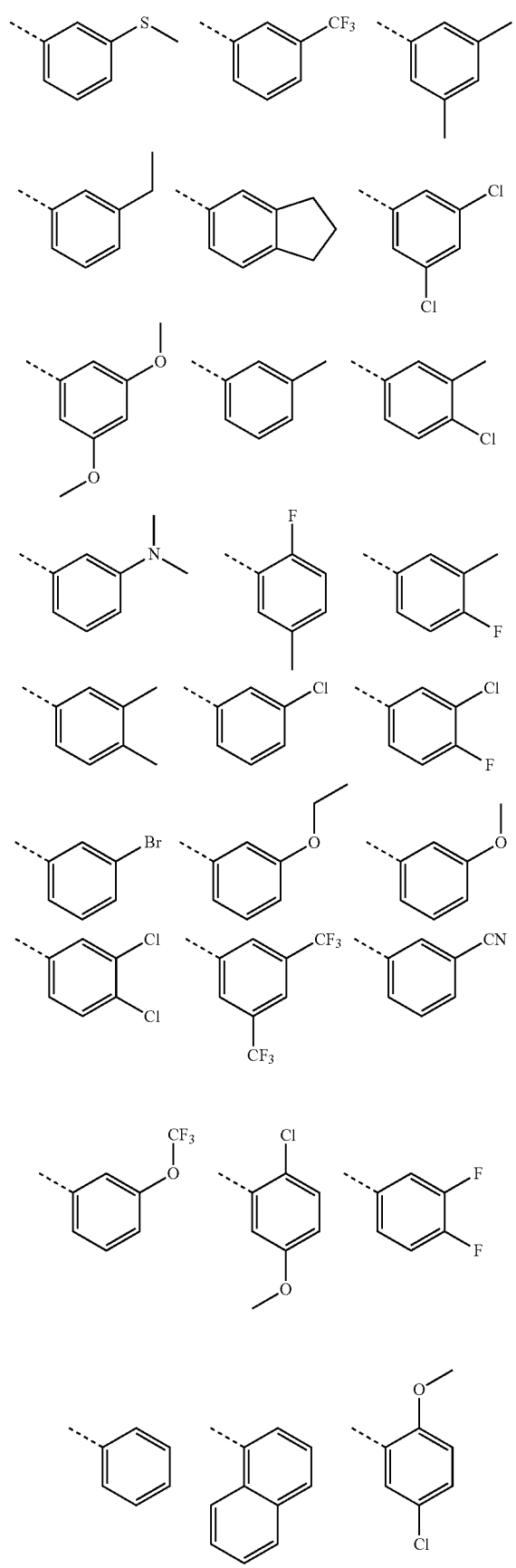

-continued

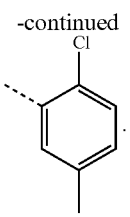

15) A further embodiment of the invention relates to compounds according to any one of embodiments 1) to 13), or pharmaceutically acceptable salts thereof, for the prevention or treatment of diseases or disorders related to the orexin system; wherein $R^2$ represents aryl which is unsubstituted, or mono-, di-, or tri-substituted (especially unsubstituted, or mono-, or di-substituted), wherein the substituents are independently selected from the group consisting of $(C_{1-4})$alkyl, $(C_{1-4})$alkoxy, halogen, $(C_{1-3})$fluoroalkyl, $(C_{1-3})$fluoroalkoxy, dimethylamino, cyano, and $(C_{1-3})$alkyl-thio-; or $R^2$ represents an indanyl group.

16) A further embodiment of the invention relates to compounds according to any one of embodiments 1) to 13), or pharmaceutically acceptable salts thereof, for the prevention or treatment of diseases or disorders related to the orexin system; wherein $R^2$ represents aryl which is mono-, or di-substituted, wherein the substituents are independently selected from the group consisting of $(C_{1-4})$alkyl, $(C_{1-4})$alkoxy, halogen, $(C_{1-3})$fluoroalkyl, $(C_{1-3})$fluoroalkoxy, and $(C_{1-3})$alkyl-thio-; or $R^2$ represents an indanyl group.

17) A further embodiment of the invention relates to compounds according to any one of embodiments 1) to 16), or pharmaceutically acceptable salts thereof, for the prevention or treatment of diseases or disorders related to the orexin system; wherein, in case $R^2$ represents phenyl, such phenyl is substituted as explicitly defined, wherein at least one substituent is attached in position 3 or in position 5 of the phenyl ring (it being well understood that positions 3 and 5 designate both meta-positions with regard to the point of attachment of the rest of the molecule to said phenyl ring).

18) A further embodiment of the invention relates to compounds according to any one of embodiments 1) to 13), or pharmaceutically acceptable salts thereof, for the prevention or treatment of diseases or disorders related to the orexin system; wherein $R^2$ represents a group selected from the group consisting of phenyl, 3-chloro-phenyl, 3-bromo-phenyl, 3-methyl-phenyl, 3-methylthio-phenyl, 2-chloro-5-methyl-phenyl, 4-chloro-3-methyl-phenyl, 2-fluoro-5-methyl-phenyl, 4-fluoro-3-methyl-phenyl, 3-ethyl-phenyl, 3,5-dimethyl-phenyl, 3,4-dimethyl-phenyl, 3,4-dichloro-phenyl, 3,5-dichloro-phenyl, 3-chloro-4-fluoro-phenyl, 3,4-difluoro-phenyl, 3-methoxy-phenyl, 3-cyano-phenyl, 5-chloro-2-methoxy-phenyl, 2-chloro-5-methoxy-phenyl, 3-ethoxy-phenyl, 3-dimethylamino-phenyl, 3-trifluoromethyl-phenyl, 3,5-dimethoxy-phenyl, 1-naphthyl, 3-trifluoromethoxy-phenyl, 3,5-bistrifluoromethyl-phenyl, and indan-5-yl.

19) A further embodiment of the invention relates to compounds according to any one of embodiments 1) to 13), or pharmaceutically acceptable salts thereof, for the prevention or treatment of diseases or disorders related to the orexin system; wherein $R^2$ represents a group selected from the group consisting of 3-chloro-phenyl, 3-bromo-phenyl, 3-methyl-phenyl, 3-methylthio-phenyl, 3-ethyl-phenyl, 3,5-dimethyl-phenyl, 3,5-dichloro-phenyl, 3-methoxy-phenyl, 3-methoxy-phenyl, 3-ethoxy-phenyl, 3-methoxy-phenyl, 3-trifluoromethyl-phenyl, 3,5-dimethoxy-phenyl, and indan-5-yl (especially 3-chloro-phenyl, 3-bromo-phenyl, 3-methylphenyl, 3-methylthio-phenyl, 3-ethyl-phenyl, 3,5-dimethyl-phenyl, 3,5-dichloro-phenyl, 3,5-dimethoxy-phenyl, and indan-5-yl).

20) A further embodiment of the invention relates to compounds according to any one of embodiments 1) to 13), or pharmaceutically acceptable salts thereof, for the prevention or treatment of diseases or disorders related to the orexin system; wherein $R^2$ represents a group selected from the group consisting of:

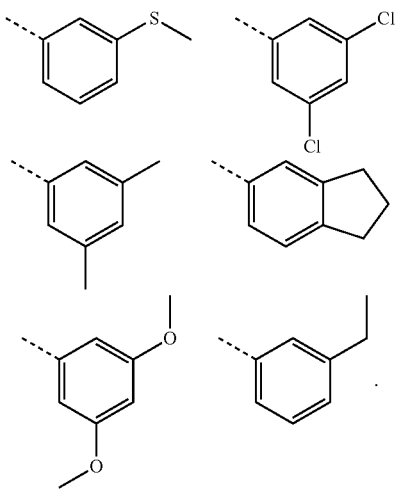

21) A further embodiment of the invention relates to compounds according to any one of embodiments 1) to 13), or pharmaceutically acceptable salts thereof, for the prevention or treatment of diseases or disorders related to the orexin system; wherein $R^2$ represents a group selected from the group consisting of 3-chloro-phenyl, 3-bromo-phenyl, 3-methyl-phenyl, 3-methylthio-phenyl, 3-ethyl-phenyl, 3,5-dimethyl-phenyl, 3,5-dichloro-phenyl, and 3,5-dimethoxy-phenyl.

22) A further embodiment of the invention relates to compounds according to any one of embodiments 1) to 13), or pharmaceutically acceptable salts thereof, for the prevention or treatment of diseases or disorders related to the orexin system; wherein $R^2$ represents a group selected from the group consisting of 3-chloro-phenyl, 3-bromo-phenyl, 3-methyl-phenyl, 3-methylthio-phenyl, and 3-ethyl-phenyl.

23) A further embodiment of the invention relates to compounds according to any one of embodiments 1) to 13), or pharmaceutically acceptable salts thereof, for the prevention or treatment of diseases or disorders related to the orexin system; wherein $R^2$ represents a group selected from the group consisting of 3,5-dimethyl-phenyl, 3,5-dichloro-phenyl, and 3,5-dimethoxy-phenyl.

24) A further embodiment of the invention relates to compounds according to any one of embodiments 1) to 13), or pharmaceutically acceptable salts thereof, for the prevention or treatment of diseases or disorders related to the orexin system; wherein $R^2$ represents 3,5-dimethyl-phenyl.

25) A further embodiment of the invention relates to compounds according to embodiment 1), or pharmaceutically acceptable salts thereof, for the prevention or treatment of diseases or disorders related to the orexin system; wherein
$R^1$ represents a group selected from the group consisting of 4-chloro-phenyl, 3-chloro-phenyl, 4-bromo-phenyl, 3-bromo-phenyl, 3-chloro-4-methyl-phenyl, 3,4-dichloro-phenyl, 3-methoxy-phenyl, 4-methoxy-phenyl, 2-methoxy-5-methyl-phenyl, 4-trifluoromethyl-phenyl, 3,4-dimethoxy-phenyl, 2-chloro-4-trifluoromethyl-phenyl, and 4-chloro-3-trifluoromethyl-phenyl; and
$R^2$ represents a group selected from the group consisting of 3-chloro-phenyl, 3-bromo-phenyl, 3-methyl-phenyl, 3-methylthio-phenyl, 3-ethyl-phenyl, 3,5-dimethyl-phenyl, 3,5-dichloro-phenyl, indan-5-yl, and 3,5-dimethoxy-phenyl.

26) A further embodiment of the invention relates to compounds according to embodiment 1), or pharmaceutically acceptable salts thereof, for the prevention or treatment of diseases or disorders related to the orexin system; wherein said compound is selected from the group consisting of:
(S)-1-(5-Bromo-thiophene-2-sulfonyl)-pyrrolidine-2-carboxylic acid (3-methylsulfanyl-phenyl)-amide;
(S)-1-(3-Methoxy-benzenesulfonyl)-pyrrolidine-2-carboxylic acid (3-methylsulfanyl-phenyl)-amide;
(S)-1-(4-Propyl-benzenesulfonyl)-pyrrolidine-2-carboxylic acid (3-methylsulfanyl-phenyl)-amide;
(S)-1-(4-Methoxy-benzenesulfonyl)-pyrrolidine-2-carboxylic acid (3-methylsulfanyl-phenyl)-amide;
(S)-1-(3-Chloro-benzenesulfonyl)-pyrrolidine-2-carboxylic acid (3-methylsulfanyl-phenyl)-amide;
(S)-1-(4-Trifluoromethyl-benzenesulfonyl)-pyrrolidine-2-carboxylic acid (3-methylsulfanyl-phenyl)-amide;
(S)-1-(4-Chloro-benzenesulfonyl)-pyrrolidine-2-carboxylic acid (3-methylsulfanyl-phenyl)-amide;
(S)-1-(3,4-Dimethoxy-benzenesulfonyl)-pyrrolidine-2-carboxylic acid (3-methylsulfanyl-phenyl)-amide;
(S)-1-(3-Bromo-benzenesulfonyl)-pyrrolidine-2-carboxylic acid (3-methylsulfanyl-phenyl)-amide;
(S)-1-(3-Chloro-4-methyl-benzenesulfonyl)-pyrrolidine-2-carboxylic acid (3-methylsulfanyl-phenyl)-amide;
(S)-1-(4-Bromo-benzenesulfonyl)-pyrrolidine-2-carboxylic acid (3-methylsulfanyl-phenyl)-amide;
(S)-1-(3,4-Dichloro-benzenesulfonyl)-pyrrolidine-2-carboxylic acid (3-methylsulfanyl-phenyl)-amide;
(S)-1-(4-Methoxy-benzenesulfonyl)-pyrrolidine-2-carboxylic acid (3,5-dichloro-phenyl)-amide;
(S)-1-(4-Methoxy-benzenesulfonyl)-pyrrolidine-2-carboxylic acid (3-trifluoromethyl-phenyl)-amide;
(S)-1-(4-Methoxy-benzenesulfonyl)-pyrrolidine-2-carboxylic acid (3-chloro-phenyl)-amide;
(S)-1-(4-Methoxy-benzenesulfonyl)-pyrrolidine-2-carboxylic acid (3-bromo-phenyl)-amide;
(S)-1-(4-Methoxy-benzenesulfonyl)-pyrrolidine-2-carboxylic acid m-tolylamide;
(S)-1-(4-Methoxy-benzenesulfonyl)-pyrrolidine-2-carboxylic acid (3-methoxy-phenyl)-amide;
(S)-1-(4-Methoxy-benzenesulfonyl)-pyrrolidine-2-carboxylic acid (3-dimethylamino-phenyl)-amide;
(S)-1-(4-Methoxy-benzenesulfonyl)-pyrrolidine-2-carboxylic acid (3,4-dimethyl-phenyl)-amide;
(S)-1-(4-Methoxy-benzenesulfonyl)-pyrrolidine-2-carboxylic acid (3,5-dimethyl-phenyl)-amide;
(S)-1-(4-Methoxy-benzenesulfonyl)-pyrrolidine-2-carboxylic acid (3,5-dimethoxy-phenyl)-amide;
(S)-1-(4-Methoxy-benzenesulfonyl)-pyrrolidine-2-carboxylic acid (3-chloro-4-fluoro-phenyl)-amide;
(S)-1-(4-Methoxy-benzenesulfonyl)-pyrrolidine-2-carboxylic acid (3-ethoxy-phenyl)-amide;
(S)-1-(4-Methoxy-benzenesulfonyl)-pyrrolidine-2-carboxylic acid indan-5-ylamide;
(S)-1-(4-Methoxy-benzenesulfonyl)-pyrrolidine-2-carboxylic acid (3-ethyl-phenyl)-amide;

(S)-1-(4-Methoxy-benzenesulfonyl)-pyrrolidine-2-carboxylic acid (4-fluoro-3-methyl-phenyl)-amide;
(S)-1-(4-Methoxy-benzenesulfonyl)-pyrrolidine-2-carboxylic acid (2-fluoro-5-methyl-phenyl)-amide;
(S)-1-(4-Methoxy-benzenesulfonyl)-pyrrolidine-2-carboxylic acid (4-chloro-3-methyl-phenyl)-amide;
(S)-1-(4-Bromo-benzenesulfonyl)-pyrrolidine-2-carboxylic acid (3,5-dimethyl-phenyl)-amide;
(S)-1-(Naphthalene-1-sulfonyl)-pyrrolidine-2-carboxylic acid (3,5-dimethyl-phenyl)-amide;
(S)-1-(Naphthalene-2-sulfonyl)-pyrrolidine-2-carboxylic acid (3,5-dimethyl-phenyl)-amide;
(S)-1-(3,4-Dimethoxy-benzenesulfonyl)-pyrrolidine-2-carboxylic acid (3,5-dimethyl-phenyl)-amide;
(S)-1-(4-Chloro-benzenesulfonyl)-pyrrolidine-2-carboxylic acid (3,5-dimethyl-phenyl)-amide;
(S)-1-(2-Methoxy-5-methyl-benzenesulfonyl)-pyrrolidine-2-carboxylic acid (3,5-dimethyl-phenyl)-amide;
(S)-1-(4-Methanesulfonyl-benzenesulfonyl)-pyrrolidine-2-carboxylic acid (3,5-dimethyl-phenyl)-amide;
(S)-1-(2-Chloro-4-trifluoromethyl-benzenesulfonyl)-pyrrolidine-2-carboxylic acid (3,5-dimethyl-phenyl)-amide;
(S)-1-(4-Chloro-3-trifluoromethyl-benzenesulfonyl)-pyrrolidine-2-carboxylic acid (3,5-dimethyl-phenyl)-amide;
(S)-1-(3,4-Dichloro-benzenesulfonyl)-pyrrolidine-2-carboxylic acid (3,5-dimethyl-phenyl)-amide; and
(S)-1-(4-Bromo-2-methyl-benzenesulfonyl)-pyrrolidine-2-carboxylic acid (3,5-dimethyl-phenyl)-amide.

27) A further embodiment of the invention relates to pharmaceutical compositions comprising
a compound of Formula (I) as defined in any one of embodiments 1) to 26), or a pharmaceutically acceptable salt thereof, and
a pharmaceutically acceptable carrier material;
for the prevention or treatment of diseases or disorders related to the orexin system.

28) A further embodiment of the invention relates to any one of embodiments 1) to 27), wherein said diseases or disorders related to the orexin system are selected from the group consisting of sleep disorders, anxiety disorders, addiction disorders, cognitive dysfunctions, mood disorders, or appetite disorders (especially sleep disorders, anxiety disorders, and addiction disorders).

In the following embodiments, compounds of the present invention which may be particularly useful as novel medicaments; especially for the prevention or treatment of diseases or disorders related to the orexin system, such as especially sleep disorders, anxiety disorders, addiction disorders, cognitive dysfunctions, mood disorders, or appetite disorders; are described.

Some compounds of formula (II) as defined below are known in the chemical abstracts databases [e.g. (S)-1-(4-chlorobenzenesulfonyl)-pyrrolidine-2-carboxylic acid-(3-methyl-phenyl)-amide (CAS Registry: 1212485-82-9); (S)-1-(4-chlorobenzenesulfonyl)-pyrrolidine-2-carboxylic acid-(3,5-dichloro-phenyl)-amide (CAS Registry: 1212428-50-6); and (S)-1-(4-chlorobenzenesulfonyl)-pyrrolidine-2-carboxylic acid-(indan-5-yl)-amide (CAS Registry: 1004949-76-1)]. Further compounds are CAS registered in racemic form. However, no pharmaceutical use of such compounds of formula (II), especially not their use as orexin receptor antagonists, is known.

29) Thus, the invention further relates to proline sulfonamide compounds of formula (I) as defined in embodiment 1), or pharmaceutically acceptable salts thereof;
wherein said compounds of formula (I) are also compounds of formula (II)

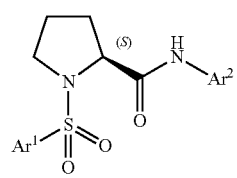

Formula (II)

wherein
the absolute configuration at the center of chirality is (S);
$Ar^1$ represents phenyl which is mono-substituted in position 3 or position 4 with chloro, bromo, methoxy, or trifluoromethyl; or di-substituted in position 3 and 4 wherein the substituents are independently selected from the group consisting of chloro, methyl, methoxy, and trifluoromethyl;
$Ar^2$ represents phenyl which is mono-substituted in position 3 with chloro, bromo, methyl, ethyl, or methylthio; or di-substituted in position 3 and 5 wherein the substituents are independently selected from the group consisting of chloro, methyl, and methoxy; or $Ar^2$ represents indan-5-yl;
for use as a medicament.

30) A further embodiment of the invention relates to compounds of formula (II) according to embodiment 29); wherein
$Ar^1$ represents a group selected from the group consisting of 4-chloro-phenyl, 3-chloro-phenyl, 4-bromo-phenyl, 3-bromo-phenyl, 3-chloro-4-methyl-phenyl, 3,4-dichloro-phenyl, 3-methoxy-phenyl, 4-methoxy-phenyl, 4-trifluoromethyl-phenyl, 3,4-dimethoxy-phenyl, and 4-chloro-3-trifluoromethyl-phenyl; and
$Ar^2$ represents a group selected from the group consisting of 3-chloro-phenyl, 3-bromo-phenyl, 3-methyl-phenyl, 3-methylthio-phenyl, 3-ethyl-phenyl, 3,5-dimethyl-phenyl, 3,5-dichloro-phenyl, indan-5-yl, and 3,5-dimethoxy-phenyl;
for use as a medicament.

31) A further embodiment of the invention relates to compounds of formula (II) according to embodiment 29); wherein
$Ar^1$ represents phenyl which is mono-substituted in position 3 or 4 with chloro, bromo, or methoxy; or di-substituted in position 3 and 4 wherein the substituents are independently selected from the group consisting of chloro, methyl, methoxy, and trifluoromethyl; and
$Ar^2$ represents phenyl which is mono-substituted in position 3 with chloro, bromo, methyl, ethyl, or methylthio-; or di-substituted in position 3 and 5 wherein the substituents are independently selected from the group consisting of chloro, methyl, and methoxy;
for use as a medicament.

32) A further embodiment of the invention relates to compounds of formula (II) according to embodiment 29); wherein
$Ar^1$ represents a group selected from the group consisting of 4-chloro-phenyl, 3-chloro-phenyl, 4-bromo-phenyl, 3-bromo-phenyl, 3-chloro-4-methyl-phenyl, 3,4-dichloro-phenyl, 3-methoxy-phenyl, 4-methoxy-phenyl, 3,4-dimethoxy-phenyl, and 4-chloro-3-trifluoromethyl-phenyl; and
$Ar^2$ represents a group selected from the group consisting of 3-chloro-phenyl, 3-bromo-phenyl, 3-methyl-phenyl, 3-methylthio-phenyl, 3-ethyl-phenyl, 3,5-dimethyl-phenyl, 3,5-dichloro-phenyl, and 3,5-dimethoxy-phenyl;
for use as a medicament.

33) A further embodiment of the invention relates to compounds of formula (II) according to any one of embodiments 29) to 32); wherein $Ar^1$ represents a group selected from the group consisting of 3-chloro-phenyl, 4-bromo-phenyl, 3-bromo-phenyl, 3-chloro-4-methyl-phenyl, 3,4-dichloro-phenyl, 3-methoxy-phenyl, 4-methoxy-phenyl, 3,4-dimethoxy-phenyl, and 4-chloro-3-trifluoromethyl-phenyl; for use as a medicament.

34) A further embodiment of the invention relates to compounds of formula (II) according to any one of embodiments 29) to 32); wherein $Ar^1$ represents 4-methoxy-phenyl; for use as a medicament.

35) A further embodiment of the invention relates to compounds of formula (II) according to any one of embodiments 29) to 34); wherein $Ar^2$ represents a group selected from the group consisting of 3-chloro-phenyl, 3-bromo-phenyl, 3-methylthio-phenyl, 3-ethyl-phenyl, 3,5-dimethyl-phenyl, and 3,5-dimethoxy-phenyl; for use as a medicament.

36) A further embodiment of the invention relates to compounds of formula (II) according to any one of embodiments 29) to 34); wherein $Ar^2$ represents a group selected from the group consisting of 3-chloro-phenyl, 3-bromo-phenyl, 3-ethyl-phenyl, 3,5-dimethyl-phenyl, and 3,5-dimethoxy-phenyl; for use as a medicament.

37) A further embodiment of the invention relates to compounds of formula (II) according to any one of embodiments 29) to 34); wherein $Ar^2$ represents 3-methylthio-phenyl; for use as a medicament.

38) A further embodiment of the invention relates to compounds of formula (II) according to any one of embodiments 29) to 34); wherein $Ar^2$ represents 3,5-dimethyl-phenyl; for use as a medicament.

39) Another embodiment relates to compounds of formula (II) according to embodiment 29), wherein said compound of formula (II) is selected from the group consisting of:
(S)-1-(3-Methoxy-benzenesulfonyl)-pyrrolidine-2-carboxylic acid (3-methylsulfanyl-phenyl)-amide;
(S)-1-(4-Methoxy-benzenesulfonyl)-pyrrolidine-2-carboxylic acid (3-methylsulfanyl-phenyl)-amide;
(S)-1-(3-Chloro-benzenesulfonyl)-pyrrolidine-2-carboxylic acid (3-methylsulfanyl-phenyl)-amide;
(S)-1-(4-Trifluoromethyl-benzenesulfonyl)-pyrrolidine-2-carboxylic acid (3-methylsulfanyl-phenyl)-amide;
(S)-1-(4-Chloro-benzenesulfonyl)-pyrrolidine-2-carboxylic acid (3-methylsulfanyl-phenyl)-amide;
(S)-1-(3,4-Dimethoxy-benzenesulfonyl)-pyrrolidine-2-carboxylic acid (3-methylsulfanyl-phenyl)-amide;
(S)-1-(3-Bromo-benzenesulfonyl)-pyrrolidine-2-carboxylic acid (3-methylsulfanyl-phenyl)-amide;
(S)-1-(3-Chloro-4-methyl-benzenesulfonyl)-pyrrolidine-2-carboxylic acid (3-methylsulfanyl-phenyl)-amide;
(S)-1-(4-Bromo-benzenesulfonyl)-pyrrolidine-2-carboxylic acid (3-methylsulfanyl-phenyl)-amide;
(S)-1-(3,4-Dichloro-benzenesulfonyl)-pyrrolidine-2-carboxylic acid (3-methylsulfanyl-phenyl)-amide;
(S)-1-(4-Methoxy-benzenesulfonyl)-pyrrolidine-2-carboxylic acid (3,5-dichloro-phenyl)-amide;
(S)-1-(4-Methoxy-benzenesulfonyl)-pyrrolidine-2-carboxylic acid (3-chloro-phenyl)-amide;
(S)-1-(4-Methoxy-benzenesulfonyl)-pyrrolidine-2-carboxylic acid (3-bromo-phenyl)-amide;
(S)-1-(4-Methoxy-benzenesulfonyl)-pyrrolidine-2-carboxylic acid m-tolylamide;
(S)-1-(4-Methoxy-benzenesulfonyl)-pyrrolidine-2-carboxylic acid (3,5-dimethyl-phenyl)-amide;
(S)-1-(4-Methoxy-benzenesulfonyl)-pyrrolidine-2-carboxylic acid (3,5-dimethoxy-phenyl)-amide;
(S)-1-(4-Methoxy-benzenesulfonyl)-pyrrolidine-2-carboxylic acid indan-5-ylamide;
(S)-1-(4-Methoxy-benzenesulfonyl)-pyrrolidine-2-carboxylic acid (3-ethyl-phenyl)-amide;
(S)-1-(4-Bromo-benzenesulfonyl)-pyrrolidine-2-carboxylic acid (3,5-dimethyl-phenyl)-amide;
(S)-1-(3,4-Dimethoxy-benzenesulfonyl)-pyrrolidine-2-carboxylic acid (3,5-dimethyl-phenyl)-amide;
(S)-1-(4-Chloro-benzenesulfonyl)-pyrrolidine-2-carboxylic acid (3,5-dimethyl-phenyl)-amide;
(S)-1-(4-Chloro-3-trifluoromethyl-benzenesulfonyl)-pyrrolidine-2-carboxylic acid (3,5-dimethyl-phenyl)-amide; and
(S)-1-(3,4-Dichloro-benzenesulfonyl)-pyrrolidine-2-carboxylic acid (3,5-dimethyl-phenyl)-amide;
for use as a medicament.

40) Another embodiment relates to the compound of formula (II) according to embodiment 29), wherein said compound of formula (II) is (S)-1-(4-Methoxy-benzenesulfonyl)-pyrrolidine-2-carboxylic acid (3,5-dimethyl-phenyl)-amide; for use as a medicament.

41) A further embodiment of the invention relates to pharmaceutical compositions comprising a compound of formula (II) as defined in any one of embodiments 29) to 40), or a pharmaceutically acceptable salt thereof, and a pharmaceutically acceptable carrier material.

Such pharmaceutical compositions according to embodiment 41) are especially useful for the prevention or treatment of diseases or disorders related to the orexin system, such as especially sleep disorders, anxiety disorders, addiction disorders, cognitive dysfunctions, mood disorders, or appetite disorders.

42) A further embodiment of the invention relates to a pharmaceutical composition according to embodiment 41), wherein said pharmaceutical composition is in form of a tablet.

43) A further embodiment of the invention relates to a pharmaceutical composition according to embodiment 41), wherein said pharmaceutical composition is in form of a capsule.

44) A further embodiment of the invention relates to a pharmaceutical composition according to any one of embodiments 41) to 43), wherein said pharmaceutical composition comprises one or more pharmaceutically acceptable carriers, wherein said pharmaceutically acceptable carriers comprise diluents such as calcium hydrogen phosphate dihydrate, partially pregelatinized maize starch, microcrystalline cellulose, mannitol, lactose monohydrate or talc; lubricants such as magnesium stearate; disintegrants such as crosscarmellose sodium; glidants such as silicon dioxide; binders such as povidone or hypromellose; capsule materials such as hydroxypropyl methylcellulose (hypromellose, HPMC); and/or surfactants such as sodium lauryl sulfate, surfactants of the Gelucire® type like Gelucire® 44/14, surfactants of the Labrafil® type, or surfactants of the Labrasol® type.

45) A further embodiment of the invention relates to a compound of formula (II) as defined in any one of embodiments 29) to 40), or a pharmaceutically acceptable salt thereof, for use in the prevention or treatment of diseases or disorders related to the orexin system.

46) A further embodiment of the invention relates to a compound of formula (II) as defined in any one of embodiments 29) to 40), or a pharmaceutically acceptable salt thereof, for use in the preparation of a medicament for the prevention or treatment of diseases or disorders related to the orexin system.

47) A further embodiment of the invention relates to pharmaceutical compositions according to any one of embodiments 41) to 44), for the prevention or treatment of diseases or disorders related to the orexin system.

48) A further embodiment of the invention relates to any one of embodiments 45) to 47), wherein said diseases or disorders related to the orexin system are selected from the group consisting of sleep disorders, anxiety disorders, addiction disorders, cognitive dysfunctions, mood disorders, or appetite disorders (especially sleep disorders, anxiety disorders, and addiction disorders).

49) A further embodiment of the invention relates to any one of embodiments 45) to 47), wherein said diseases or disorders related to the orexin system are selected from the group consisting of sleep disorders selected from the group consisting of dyssomnias, parasomnias, sleep disorders associated with a general medical condition and substance-induced sleep disorders; anxiety disorders; and addiction disorders.

50) A further embodiment of the invention relates to products or kits of parts comprising a compound of formula (II) as defined in any one of embodiments 29) to 40), or a pharmaceutically acceptable salt thereof, in combination with another pharmaceutically active ingredient; for the prevention or treatment of diseases or disorders related to the orexin system, such as especially sleep disorders, anxiety disorders, addiction disorders, cognitive dysfunctions, mood disorders, or appetite disorders.

51) A further embodiment of the invention relates to a pharmaceutical composition according to any one of embodiments 41) to 44), comprising a compound of formula (II) as defined in any one of embodiments 29) to 40), or a pharmaceutically acceptable salt thereof, in combination with another pharmaceutically active ingredient; for the prevention or treatment of diseases or disorders related to the orexin system, such as especially sleep disorders, anxiety disorders, addiction disorders, cognitive dysfunctions, mood disorders, or appetite disorders.

The present invention also includes isotope labeled, especially $^2$H (deuterium) labeled compounds of formula (I) or (II) as defined in any one of embodiments 1) to 40), which compounds are identical to the compounds of formula (I) except that one or more atoms have each been replaced by an atom having the same atomic number but an atomic mass different from the atomic mass usually found in nature. Isotope labeled, especially $^2$H (deuterium) labeled compounds of formula (I) or (II) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) or (II) are not isotope labeled, or they are labeled only with one or more deuterium atoms. In a sub-embodiment, the compounds of formula (I) or (II) are not isotope labeled at all. Isotope labeled compounds of formula (I) or (II) may be prepared in analogy to the methods described hereinafter, but using the appropriate isotope variation of suitable reagents or starting materials.

The compounds of formula (I) may contain one or more stereogenic or asymmetric centers, such as one or more asymmetrically substituted carbon atoms. The compounds of formula (I) may thus be present as mixtures of stereoisomers or preferably as pure stereoisomers. Mixtures of stereoisomers may be separated in a manner known to a person skilled in the art. It is well understood that the compounds of formula (I) and (II) have the absolute configuration (S) at the chiral carbon atom of the pyrrolidine ring to which the —CO—NH—$R^2$ group is attached.

Any reference to compounds of formula (I) or (II) is to be understood as referring also to the pharmaceutically acceptable salts of such compounds, as appropriate and expedient.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

The compounds of formula (I) or (II) and their pharmaceutically acceptable salts can be used as medicaments, e.g. in the form of pharmaceutical compositions for enteral (such especially oral) or parenteral administration (including topical application or inhalation).

A further aspect of the invention are pharmaceutical compositions comprising a compound of formula (I) or (II), or a pharmaceutically acceptable salt thereof, and a pharmaceutically acceptable excipient/carrier material. Such compositions are especially useful for the prevention or treatment of diseases or disorders related to the orexin system.

The production of the pharmaceutical compositions can be effected in a manner which will be familiar to any person skilled in the art (see for example Mark Gibson, Editor, Pharmaceutical Preformulation and Formulation, IHS Health Group, Englewood, Colo., USA, 2001; Remington, *The Science and Practice of Pharmacy*, 20th Edition, Philadelphia College of Pharmacy and Science) by bringing the described compounds of formula (I) and their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein, comprising administering to a subject a pharmaceutically active amount of a compound of formula (I) or (II).

In a preferred embodiment of the invention, the administered amount is comprised between 1 mg and 1000 mg per day, particularly between 5 mg and 500 mg per day, more particularly between 25 mg and 400 mg per day, especially between 50 mg and 200 mg per day.

For avoidance of any doubt, if compounds are described as useful for the prevention or treatment of certain diseases or disorders, such compounds are likewise suitable for use in the preparation of a medicament for the prevention or treatment of said diseases or disorders.

The compounds according to formulae (I) and (II) are useful as medicaments, especially for the prevention or treatment of diseases or disorders related to the orexin system.

Such diseases or disorders related to the orexin system are diseases or disorders where an antagonist of a human orexin receptor is required, notably mental health diseases or disorders relating to orexinergic dysfunctions. The above mentioned diseases or disorders may in particular be defined as comprising sleep disorders, anxiety disorders, addiction disorders, cognitive dysfunctions, mood disorders, or appetite disorders. Especially, the above mentioned diseases or disorders comprise sleep disorders, anxiety disorders, and addiction disorders.

Sleep disorders comprise dyssomnias, parasomnias, sleep disorders associated with a general medical condition and substance-induced sleep disorders. In particular, dyssomnias include intrinsic sleep disorders (especially insomnias, breathing-related sleep disorders, periodic limb movement disorder, and restless leg syndrome), extrinsic sleep disorders, and circadian-rythm sleep disorders. Dyssomnias notably include insomnia, primary insomnia, idiopathic insomnia, insomnias associated with depression, emotional/mood disorders, aging, Alzheimer's disease or cognitive impairment; REM sleep interruptions; breathing-related sleep disorders; sleep apnea; periodic limb movement disorder (nocturnal myoclonus), restless leg syndrome, circadian rhythm sleep disorder; shift work sleep disorder; and jet-lag syndrome. Parasomnias include arousal disorders and sleep-wake transition disorders; notably parasomnias include nightmare disorder, sleep terror disorder, and sleepwalking disorder. Sleep disorders associated with a general medical condition are in particular sleep disorders associated with diseases such as mental disorders, neurological disorders, neuropathic pain, and heart and lung diseases. Substance-induced sleep disorders include especially the subtypes insomnia type, parasomnia type and mixed type, and notably include conditions due to drugs which cause reductions in REM sleep as a side effect. Sleep disorders especially include all types of insomnias, sleep-related dystonias; restless leg syndrome; sleep apneas; jet-lag syndrome; shift work sleep disorder, delayed or advanced sleep phase syndrome, or insomnias related to psychiatric disorders. In addition, sleep disorders further include sleep disorders associated with aging; intermittent treatment of chronic insomnia; situational transient insomnia (new environment, noise) or short-term insomnia due to stress; grief; pain or illness.

Anxiety disorders can be distinguished by the primary object or specificity of threat, ranging from rather diffuse as in generalized anxiety disorder, to circumscribed as encountered in phobic anxieties (PHOBs) or post-traumatic stress disorders (PTSDs). Anxiety disorders may, thus, be defined as comprising generalized anxiety disorders (GAD), obsessive compulsive disorders (OCDs), acute stress disorders, post-traumatic stress disorders (PTSDs), panic anxiety disorders (PADs) including panic attacks, phobic anxieties (PHOBs), specific phobia, social phobia (social anxiety disorder), avoidance, somatoform disorders including hypochondriasis, separation anxiety disorder, anxiety disorders due to a general medical condition, and substance induced anxiety disorders. In a sub-embodiment, particular examples of circumscribed threat induced anxiety disorders are phobic anxieties or post-traumatic stress disorders. Anxiety disorders especially include generalized anxiety disorders, post-traumatic stress disorders, obsessive compulsive disorders, panic attacks, phobic anxieties, and avoidance.

Addiction disorders may be defined as addictions to one or more rewarding stimuli, notably to one rewarding stimulus. Such rewarding stimuli may be of either natural or synthetic origin. Examples of such rewarding stimuli are substances/drugs {of either natural or synthetic origin; such as cocaine, amphetamines, opiates [of natural or (semi-)synthetic origin such as morphine or heroin], cannabis, ethanol, mescaline, nicotine, and the like}, which substances/drugs may be consumed alone or in combination; or other rewarding stimuli {of either natural origin (such as food, sweet, fat, or sex, and the like), or synthetic origin [such as gambling, or internet/IT (such as immoderate gaming, or inappropriate involvement in online social networking sites or blogging), and the like]}. In a sub-embodiment, addiction disorders relating to psychoactive substance use, abuse, seeking and reinstatement are defined as all types of psychological or physical addictions and their related tolerance and dependence components. Substance-related addiction disorders especially include substance use disorders such as substance dependence, substance craving and substance abuse; substance-induced disorders such as substance intoxication, substance withdrawal, and substance-induced delirium. The expression "prevention or treatment of addictions" (i.e. preventive or curative treatment of patients who have been diagnosed as having an addiction, or as being at risk of developing addictions) refers to diminishing addictions, notably diminishing the onset of addictions, to weakening their maintenance, to facilitating withdrawal, to facilitating abstinence, or to attenuating, decreasing or preventing the occurrence of reinstatement of addiction (especially to diminishing the onset of addictions, to facilitating withdrawal, or to attenuating, decreasing or preventing the occurrence of reinstatement of addiction).

Appetite disorders comprise eating disorders and drinking disorders. Eating disorders may be defined as comprising eating disorders associated with excessive food intake and complications associated therewith; anorexias; compulsive eating disorders; obesity (due to any cause, whether genetic or environmental); obesity-related disorders including overeating and obesity observed in Type 2 (non-insulin-dependent) diabetes patients; bulimias including bulimia nervosa; cachexia; and binge eating disorder. Particular eating disorders comprise metabolic dysfunction; dysregulated appetite control; compulsive obesities; bulimia or anorexia nervosa. In a sub-embodiment, eating disorders may be defined as especially comprising anorexia nervosa, bulimia, cachexia, binge eating disorder, or compulsive obesities. Drinking disorders include polydipsias in psychiatric disorders and all other types of excessive fluid intake. Pathologically modified food intake may result from disturbed appetite (attraction or aversion for food); altered energy balance (intake vs. expenditure); disturbed perception of food quality (high fat or carbohydrates, high palatability); disturbed food availability (unrestricted diet or deprivation) or disrupted water balance.

Cognitive dysfunctions include deficits in attention, learning and especially memory functions occurring transiently or chronically in psychiatric, neurologic, neurodegenerative, cardiovascular and immune disorders, and also occurring transiently or chronically in the normal, healthy, young, adult, or especially aging population. Cognitive dysfunctions especially relate to the enhancement or maintenance of memory in patients who have been diagnosed as having, or being at risk of developing, diseases or disorders in which diminished memory (notably declarative or procedural) is a symptom [in particular dementias such as frontotemporal dementia, or dementia with Lewy bodies, or (especially) Alzheimer's disease]. Especially, the term "prevention or treatment of cognitive dysfunctions" relates to the enhancement or maintenance of memory in patients who have a clinical manifestation of a cognitive dysfunction, especially expressed as a deficit of declarative memory, linked to dementias such as frontotemporal dementia, or dementia with Lewy bodies, or (especially) Alzheimer's disease. Furthermore, the term "prevention or treatment of cognitive dysfunctions" also relates to improving memory consolidation in any of the above mentioned patient populations.

Mood disorders include major depressive episode, manic episode, mixed episode and hypomanic episode; depressive disorders including major depressive disorder, dysthymic disorders; bipolar disorders including bipolar I disorder, bipolar II disorder (recurrent major depressive episodes with hypomanic episodes), cyclothymic disorder; mood disorders including mood disorder due to a general medical condition (including the subtypes with depressive features, with major depressive-like episode, with manic features, and with mixed features), substance-induced mood disorder (including the subtypes with depressive features, with manic features, and with mixed features). Such mood disorders are especially major depressive episode, major depressive disorder, mood disorder due to a general medical condition; and substance-induced mood disorder.

In addition, further diseases related to the orexin system are selected from treating, controlling, ameliorating or reducing the risk of epilepsy, including absence epilepsy; treating or controlling pain, including neuropathic pain; treating or controlling Parkinson's disease; treating or controlling psychosis including acute mania and bipolar disorder; treating or controlling stroke, particularly ischemic or haemorrhagic stroke; blocking an emetic response i.e. nausea and vomiting; treating or controlling agitation, in isolation or co-morbid with another medical condition.

In the context of the present invention, it is to be understood that, in case certain environmental conditions such as stress or fear (wherein stress may be of social origin (e.g. social stress) or of physical origin (e.g. physical stress), including stress caused by fear) facilitate or precipitate any of the disorders or diseases as defined before, the present compounds may be particularly useful for the treatment of such environmentally conditioned disorder or disease.

In further embodiment, diseases or disorders related to the orexin system are selected from the group consisting of sleep disorders that comprises all types of insomnias, sleep-related dystonias, restless leg syndrome, sleep apneas, jet-lag syndrome, shift-work syndrome, delayed or advanced sleep phase syndrome or insomnias related to psychiatric disorders (notably all types of insomnias comprising sleep disorders associated with aging; intermittent treatment of chronic insomnia; situational transient insomnia (new environment, noise) or short-term insomnia due to stress; grief; pain or illness; especially primary insomnia); stress-related syndromes including post-traumatic stress disorders as well as other types and subtypes of anxiety disorders such as generalized anxiety, obsessive compulsive disorder, panic attacks and all types of phobic anxiety and avoidance; eating disorders that comprise metabolic dysfunction; dysregulated appetite control; compulsive obesities; bulimia or anorexia nervosa; all types of addictions (especially psychoactive substance use, abuse, seeking and reinstatement) that comprise all types of psychological or physical addictions and their related tolerance and dependence components; and cognitive dysfunctions that comprise all types of attention, learning and memory functions occurring transiently or chronically in the normal, healthy, young, adult or aging population, and also occurring transiently or chronically in psychiatric, neurologic, cardiovascular and immune disorders.

Besides, any characteristics described in this invention for the compounds of formula (I) (whether for the compounds themselves, salts thereof, compositions containing the compounds or salts thereof, uses of the compounds or salts thereof, etc.) apply mutatis mutandis to compounds of formula (II).

Preparation of Compounds of Formula (I) or (II):

A further object of the invention is a process for the preparation of compounds of formula (I). Compounds according to formula (I) of the present invention are prepared according to the general sequence of reactions outlined in the schemes below wherein $R^1$ and $R^2$ are as defined for formula (I). Compounds of formula (II) may be obtained in analogy. The compounds obtained may also be converted into pharmaceutically acceptable salts in a manner known per se. Starting materials used for the preparation of proline sulfonamide derivatives of formula (I) or formula (II) are aryl sulfonyl chlorides and anilines; both of which are well known in the art and usually commercially available.

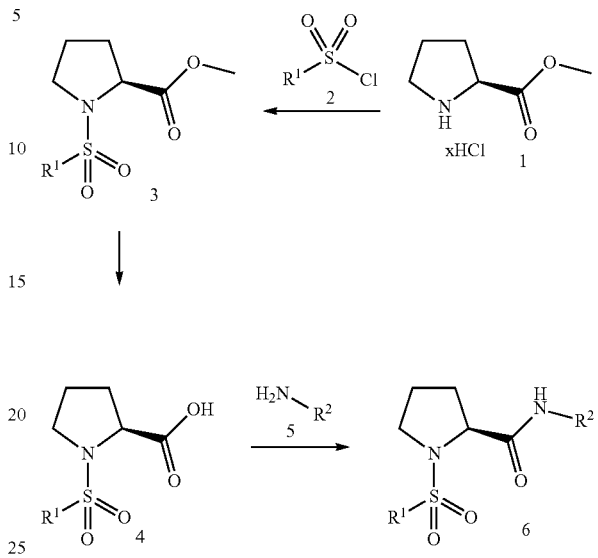

Scheme 1: Preparation of Compounds of Formula (I), Method A

The synthesis of the proline sulfonamide derivatives may be achieved by reacting commercially available L-proline methylester hydrochloride (1) in a solvent like MeCN or DCM in the presence of a base such as DIPEA or N-methylmorpholine with a sulfonylchloride 2 at rt followed by aq. work-up and purification to give the intermediate L-proline sulfonamide methyl ester 3. Ester hydrolysis may be achieved for example by dissolving derivatives 3 in THF/methanol=1/1 followed by the addition of 2 equivalents of aq. 1M NaOH solution at rt.

The crude acid is obtained after aq. work-up and may be purified by crystallization to give the pure L-proline sulfonamide carboxylic acid derivative 4, which is dissolved in a solvent such as DCM and treated with a base such as $NEt_3$ or N-methyl morpholine followed by the addition of an activating agent such as ethyl chloroformate and, subsequently, 1.2 equivalents of the aniline derivative 5. Final compounds 6 may be obtained after standard aq. work-up and chromatographic purification.

Alternatively, compounds of formula (I) may be obtained according to the procedure shown in scheme 2.

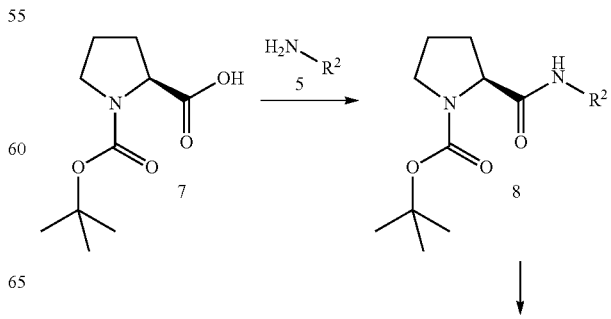

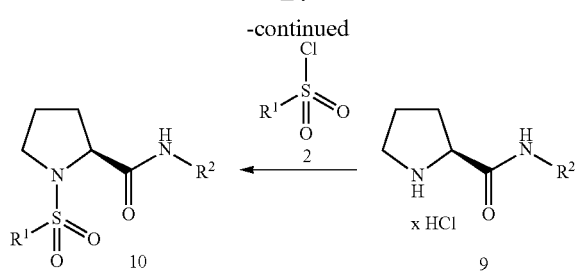

Scheme 2: Preparation of Compounds of Formula (I), Method B

The preparation of compounds of formula (I) can alternatively be carried out as depicted in scheme 2, starting from Boc-L-proline (7) which is dissolved in a solvent such as DCM or MeCN followed by the addition of a base such as NEt₃ or DIPEA or N-methyl morpholine, the activating agent ethyl chloroformate, and the aniline derivative 5. The pure Boc-protected L-proline anilides 8 may be isolated after aq. work-up and chromatographic purification. Compounds 9 are obtained by treating compounds 8 with 4M HCl in dioxane at rt. Final compounds 10 may be prepared by reacting the precursors 9 in a solvent such as MeCN or DCM in the presence of a base e.g. DIPEA or N-methylmorpholine with a sulfonylchloride 2 at rt, followed by aq. work-up and purification.

| Experimental section: Abbrevations (as used herein and in the description above): | |
|---|---|
| aq. | aqueous |
| BSA | Bovine serum albumine |
| CC | column chromatography on silica gel |
| CHO | Chinese hamster ovary |
| DCM | dichloromethane |
| DIPEA | n-ethyl-di-isopropylamine |
| DMSO | dimethylsulfoxide |
| ether | diethyl ether |
| EtOAc | ethyl acetate |
| EtOH | ethanol |
| FCS | Foatal calf serum |
| FLIPR | Fluorescent imaging plate reader |
| HBSS | Hank's balanced salt solution |
| HEPES | 4-(2-hydroxyethyl)-piperazine-1-ethanesulfonic acid |
| HPLC | high performance liquid chromatography |
| LC | liquid chromatography |

| Experimental section: Abbrevations (as used herein and in the description above): | |
|---|---|
| M | molarity [mol L$^{-1}$] |
| MeCN | acetonitrile |
| MeOH | methanol |
| MS | mass spectroscopy |
| N | normality |
| NEt₃ | triethylamine |
| rt | room temperature |
| sat. | saturated |
| TFA | trifluoroacetic acid |
| THF | tetrahydrofuran |
| UV | ultraviolet |

I—Chemistry

The following examples illustrate the preparation of biologically active compounds of the invention but do not at all limit the scope thereof.

All temperatures are stated in ° C.
Intermediates are Characterized by:
LC-MS: Agilent 1100 series with DAD and MS detection (MS: Finnigan single quadrupole); columns (4.6×50 mm, 5 μm): Zorbax SB-AQ, Zorbax Extend C18 or Waters XBridge C18; conditions (if not otherwise stated the acidic gradient is used):

acidic: eluent A: MeCN, eluent B: TFA in water (0.4 mL/L), 5% to 95% MeCN, flow rate 4.5 mL/min; $t_R$ is given in min.

Compounds are purified by column chromatography on silica gel (CC) or by preparative HPLC using RP-C₁₈ based columns with MeCN/water gradients and ammonia additives.
Final Compounds are Characterized by:
Conditions and Intruments:
LC-MS-conditions: Analytical. Pump: Waters Acquity Binary, Solvent Manager, MS: Waters SQ Detector, DAD: Acquity UPLC PDA Detector, ELSD: Acquity UPLC ELSD. Column: Acquity UPLC BEH C18 1.7 mm 2.1×50 mm from Waters, thermostated in the Acquity UPLC Column Manager at 50° C. Eluents: A1: H2O+0.05% FA; B1: AcCN+0.05% FA; A2: H2O+0.05% TFA; B2: AcCN+0.05% TFA. Method: Gradient: 2% B 98% B over 1.5 min. Flow: 1.2 mL/min. Detection: UV 214 nm and ELSD, and MS, $t_R$ is given in min.

A. General Methods for the Preparation of Compounds of Formula (I)

A.1. Method A

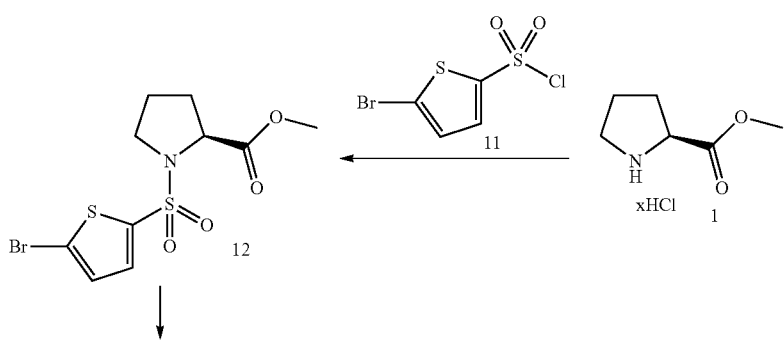

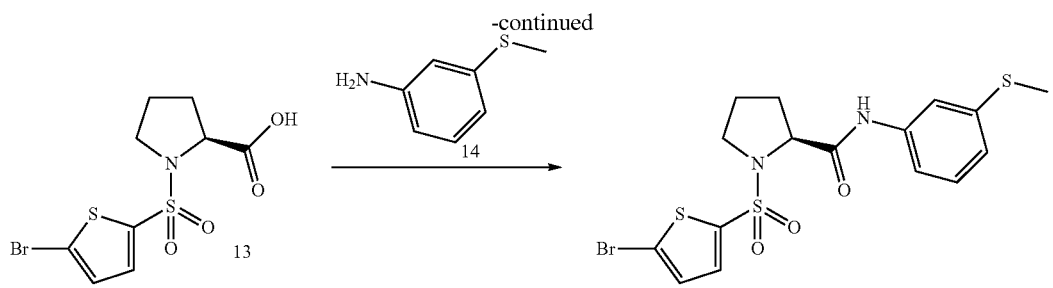

Step 1: Commercially available L-proline-methylester hydrochloride (3.0 g; 18.1 mmol) (1) is dissolved in DCM (50 ml) at rt and DIPEA (7.03 g; 54.3 mmol) is slowly added over 10 minutes followed by the careful addition of commercially available 5-bromo-thiophene-2-sulfonyl chloride (4.7 g; 18.1 mmol). The reaction mixture is stirred for 12 h at rt followed by the addition of sat. aq. NH$_4$Cl solution (100 ml) and the extraction of the product with DCM (3×50 ml). The combined organic layers are dried over MgSO$_4$, filtered and concentrated under reduced pressure to give 6.35 g (98.9%) of 12 which was used in the next step without further purification. LC-MS: $t_R$=0.97 min; [M+H]$^+$=354.19.

Step 2: Compound 12 (6.35 g; 17.93 mmol) is dissolved in MeOH (40 ml) and THF (43 ml) followed by the addition of 1M aq. NaOH solution (37 ml; 37 mmol). The reaction mixture is stirred for 12 h at rt. The organic solvents are removed under reduced pressure. The residual aq. layer is acidified by the addition of 2M aq. HCl to pH 1 to 2. The product is extracted with DCM (3×50 ml). The combined organic layers are dried over MgSO$_4$, filtered and the solvent is removed under reduced pressure to give 5.67 g (93%) of compound 13 as a white solid. LC-MS: $t_R$=0.86 min; [M+H]$^+$=340.08.

Step 3: The carboxylic acid 13 (0.672 g; 1.95 mmol) and commercially available 3-methylthioaniline (14, 0.25 g; 1.8 mmol) are dissolved in dry pyridine (15 ml) and cooled to 0° C. followed by the addition of POCl$_3$ (0.303 g; 1.98 mmol). The cooling bath is removed and stirring at rt is continued for 12 hours. The reaction mixture is concentrated under reduced pressure. The residue is dissolved in EtOAc (50 ml) and washed with brine (3×50 ml). The organic layer is dried over MgSO$_4$, filtered and the solvent is removed under reduced pressure. The crude product is purified by CC (heptanes/ETOAc=7/3) to give 0.683 g (82.4%) of (S)-1-(5-Bromo-thiophene-2-sulfonyl)-pyrrolidine-2-carboxylic acid (3-methylsulfanyl-phenyl)-amide (Example 1). LC-MS: $t_R$=1.06 min; [M+H]$^+$=462.6.

A.2. Method B

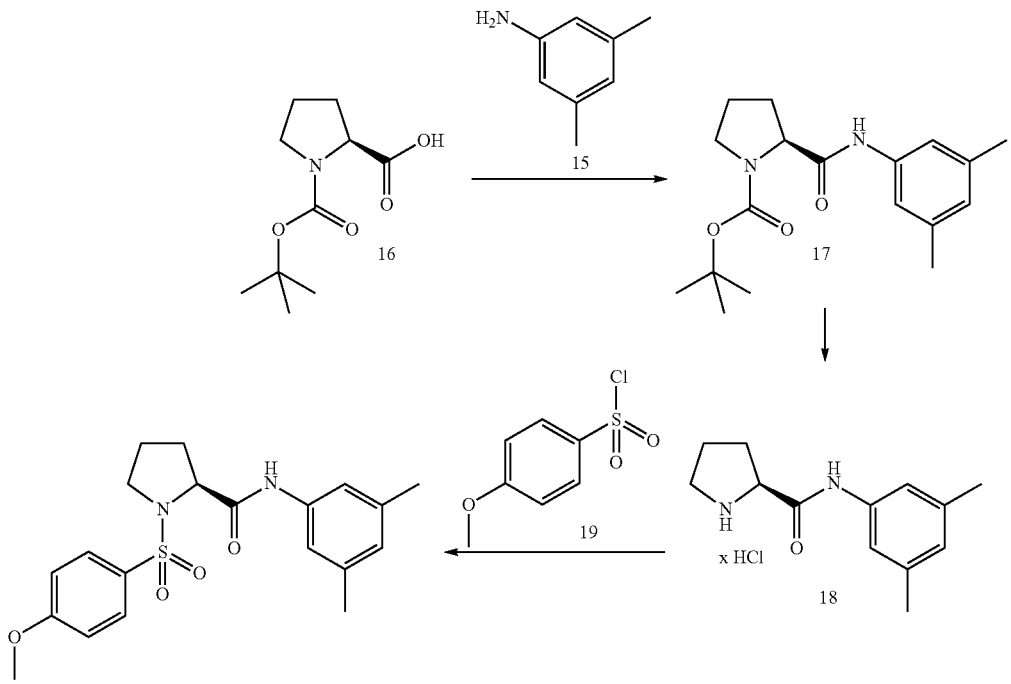

Step 1: Commercially available Boc-L-proline (16, 2.3 g; 10.7 mmol) is dissolved in DCM (20 ml) and cooled to 0° C. followed by the addition of NEt$_3$ (1.12 g; 11.22 mmol) and ethyl chloroformate (1.22 g; 11.22 mmol) and finally commercially available 3,5-dimethylaniline (15) (1.36 g; 11.22 mmol). The reaction mixture is stirred at rt for 60 minutes. Brine (50 ml) is added and the organic layer is separated. The aq. layer is extracted with DCM (2×30 ml). The combined organic layers are dried over MgSO$_4$, filtered and the solvent is removed under reduced pressure to give 4.07 g of crude (S)-tert-butyl 2-((3,5-dimethylphenyl)carbamoyl)pyrrolidine-1-carboxylate (17) which is used in the next step without further purification. LC-MS: $t_R$=0.81 min; [M+H]$^+$=319.11.

Step 2: Crude (S)-tert-butyl 2-((3,5-dimethylphenyl)carbamoyl)pyrrolidine-1-carboxylate (17, 4.07 g; 10.7 mmol) is dissolved in dioxane (15 ml) followed by the addition of 4M HCl in dioxane (60 ml) Stirring at rt is continued for 30 minutes. The solvent is evaporated under reduced pressure. The residue is taken up into ether which caused the formation of a white precipitate which was filtered off, washed with ether and dried at high vacuum to give 3.299 g (quantitative yield) of (S)—N-(3,5-dimethylphenyl)pyrrolidine-2-carboxamide hydrochloride (18) as a white solid. LC-MS: $t_R$=0.51 min; [M+H]$^+$=219.07.

Step 3: (S)—N-(3,5-dimethylphenyl)pyrrolidine-2-carboxamide hydrochloride (18, 3.299 g; 10.7 mmol) is dissolved in MeCN (40 ml) at rt and DIPEA (4.4 g; 34 mmol) is slowly added over 10 minutes followed by the careful addition of commercially available 4-methoxybenzenesulfonyl chloride (19, 2.8 g; 13.6 mmol). The reaction mixture is stirred for 12 h at rt followed by the addition of brine (50 ml) and the extraction of the product with DCM (3×35 ml). The combined organic layers are dried over MgSO$_4$, filtered and concentrated under reduced pressure to give 3.95 g (95%) of (S)—N-(3,5-dimethylphenyl)-1-((4-methoxyphenyl)sulfonyl)-pyrrolidine-2-carboxamide (Example 26) as amorphous solid. LC-MS: $t_R$=0.83 min; [M+H]$^+$=389.3.

B. Examples

The example compounds listed in the table 1 below have been prepared according to the method A or B above by using the appropriate commercially available amine and sulfonyl chloride derivatives as starting materials.

To further characterize the compounds, antagonistic activities on both orexin receptors have been measured for each example compound using the following procedure:

In Vitro Assay: Intracellular Calcium Measurements:

Chinese hamster ovary (CHO) cells expressing the human orexin-1 receptor and the human orexin-2 receptor, respectively, are grown in culture medium (Ham F-12 with L-Glutamine) containing 300 µg/ml G418, 100 U/ml penicillin, 100 µg/ml streptomycin and 10% heat inactivated fetal calf serum (FCS). The cells are seeded at 20'000 cells/well into 384-well black clear bottom sterile plates (Greiner). The seeded plates are incubated overnight at 37° C. in 5% CO$_2$.

Human orexin-A as an agonist is prepared as 1 mM stock solution in MeOH: water (1:1), diluted in HBSS containing 0.1% bovine serum albumin (BSA), NaHCO$_3$: 0.375 g/l and 20 mM HEPES for use in the assay at a final concentration of 3 nM.

Antagonists are prepared as 10 mM stock solution in DMSO, then diluted in 384-well plates using DMSO followed by a transfer of the dilutions into in HBSS containing 0.1% bovine serum albumin (BSA), NaHCO$_3$: 0.375 g/l and 20 mM HEPES. On the day of the assay, 50 µl of staining buffer (HBSS containing 1% FCS, 20 mM HEPES, NaHCO$_3$: 0.375 g/l, 5 mM probenecid (Sigma) and 3 µM of the fluorescent calcium indicator fluo-4 AM (1 mM stock solution in DMSO, containing 10% pluronic) is added to each well. The 384-well cell-plates are incubated for 50 min at 37° C. in 5% CO$_2$ followed by equilibration at RT for 30 min before measurement.

Within the Fluorescent Imaging Plate Reader (FLIPR Tetra, Molecular Devices), antagonists are added to the plate in a volume of 10 µl/well, incubated for 10 min or (where explicitly indicated) for 120 min and finally 10 µl/well of agonist is added. Fluorescence is measured for each well at 1 second intervals, and the height of each fluorescence peak is compared to the height of the fluorescence peak induced by 3 nM orexin-A with vehicle in place of antagonist. The IC$_{50}$ value (the concentration of compound needed to inhibit 50% of the agonistic response) is determined and may be normalized using the obtained IC$_{50}$ value of a on-plate reference compound. Optimized conditions were achieved by adjustment of pipetting speed and cell splitting regime. The calculated IC$_{50}$ values may fluctuate depending on the daily cellular assay performance. Fluctuations of this kind are known to those skilled in the art.

TABLE 1

Example compounds and characterization

| Example No | Chemical Name | LC-MS $t_R$ in min; [M + H]$^+$ | IC$_{50}$Ox1 [nM] | IC$_{50}$Ox2 [nM] |
|---|---|---|---|---|
| 1 | (S)-1-(5-Bromo-thiophene-2-sulfonyl)-pyrrolidine-2-carboxylic acid (3-methylsulfanyl-phenyl)-amide | 0.86; 461.1 | 20 *[2] | 10 *[2] |
| 2 | (S)-1-(5-Bromo-thiophene-2-sulfonyl)-pyrrolidine-2-carboxylic acid (3-trifluoromethoxy-phenyl)-amide | 0.92; 499.1 | 149 | 104 |
| 3 | (S)-1-(3-Methoxy-benzenesulfonyl)-pyrrolidine-2-carboxylic acid (3-methylsulfanyl-phenyl)-amide | 0.81; 407.2 | 28 | 8 |
| 4 | (S)-1-(4-Propyl-benzenesulfonyl)-pyrrolidine-2-carboxylic acid (3-methylsulfanyl-phenyl)-amide | 0.92; 419.3 | 91 | 47 |
| 5 | (S)-1-(4-Methyl-3,4-dihydro-2H-benzo[1,4]oxazine-7-sulfonyl)-pyrrolidine-2-carboxylic acid (3-methylsulfanyl-phenyl)-amide | 0.83; 447.6 | 128 | 27 |
| 6 | (S)-1-(4-Methoxy-benzenesulfonyl)-pyrrolidine-2-carboxylic acid (3-methylsulfanyl-phenyl)-amide | 0.80; 407.3 | 21 *[3] | 3 *[3] |
| 7 | (S)-1-(3-Chloro-benzenesulfonyl)-pyrrolidine-2-carboxylic acid (3-methylsulfanyl-phenyl)-amide | 0.85; 411.2 | 8 | 2 |
| 8 | (S)-1-(4-Trifluoromethyl-benzenesulfonyl)-pyrrolidine-2-carboxylic acid (3-methylsulfanyl-phenyl)-amide | 0.88; 445.2 | 63 | 17 |
| 9 | (S)-1-(4-Chloro-benzenesulfonyl)-pyrrolidine-2-carboxylic acid (3-methylsulfanyl-phenyl)-amide | 0.85; 411.2 | 15 | 9 |
| 10 | (S)-1-(3,4-Dimethoxy-benzenesulfonyl)-pyrrolidine-2-carboxylic acid (3-methylsulfanyl-phenyl)-amide | 0.77; 437.3 | 57 | 3 |
| 11 | (S)-1-(3-Bromo-benzenesulfonyl)-pyrrolidine-2-carboxylic acid (3-methylsulfanyl-phenyl)-amide | 0.86; 455.1 | 7 | 2 |

TABLE 1-continued

Example compounds and characterization

| Example No | Chemical Name | LC-MS $t_R$ in min; $[M + H]^+$ | $IC_{50}Ox1$ [nM] | $IC_{50}Ox2$ [nM] |
|---|---|---|---|---|
| 12 | (S)-1-(3-Chloro-4-methyl-benzenesulfonyl)-pyrrolidine-2-carboxylic acid (3-methylsulfanyl-phenyl)-amide | 0.89; 425.2 | 5 *2 | 3 *2 |
| 13 | (S)-1-(4-Bromo-benzenesulfonyl)-pyrrolidine-2-carboxylic acid (3-methylsulfanyl-phenyl)-amide | 0.86; 455.2 | 22 | 10 |
| 14 | (S)-1-(3,4-Dichloro-benzenesulfonyl)-pyrrolidine-2-carboxylic acid (3-methylsulfanyl-phenyl)-amide | 0.90; 445.2 | 7 *2 | 2 *2 |
| 15 | (S)-1-(5-Bromo-thiophene-2-sulfonyl)-pyrrolidine-2-carboxylic acid phenylamide | 0.81; 415.1 | 333 | 164 |
| 16 | (S)-1-(4-Methoxy-benzenesulfonyl)-pyrrolidine-2-carboxylic acid (3,5-dichloro-phenyl)-amide | 0.90; 429.2 | 64 *2 | 20 *2 |
| 17 | (S)-1-(4-Methoxy-benzenesulfonyl)-pyrrolidine-2-carboxylic acid (3-trifluoromethyl-phenyl)-amide | 0.84; 429.2 | 55 *2 | 9 *2 |
| 18 | (S)-1-(4-Methoxy-benzenesulfonyl)-pyrrolidine-2-carboxylic acid (3-chloro-phenyl)-amide | 0.82; 395.2 | 83 | 31 |
| 19 | (S)-1-(4-Methoxy-benzenesulfonyl)-pyrrolidine-2-carboxylic acid (3-bromo-phenyl)-amide | 0.83; 439.1 | 79 | 37 |
| 20 | (S)-1-(4-Methoxy-benzenesulfonyl)-pyrrolidine-2-carboxylic acid m-tolylamide | 0.78; 375.3 | 214 | 17 |
| 21 | (S)-1-(4-Methoxy-benzenesulfonyl)-pyrrolidine-2-carboxylic acid (3-methoxy-phenyl)-amide | 0.74; 391.3 | 182 | 47 |
| 22 | (S)-1-(4-Methoxy-benzenesulfonyl)-pyrrolidine-2-carboxylic acid (3-dimethylamino-phenyl)-amide | 0.66; 404.3 | 234 | 19 |
| 23 | (S)-1-(4-Methoxy-benzenesulfonyl)-pyrrolidine-2-carboxylic acid (3,4-dimethyl-phenyl)-amide | 0.82; 389.3 | 174 | 29 |
| 24 | (S)-1-(4-Methoxy-benzenesulfonyl)-pyrrolidine-2-carboxylic acid naphthalen-1-ylamide | 0.80; 411.3 | 269 | 171 |
| 25 | (S)-1-(4-Methoxy-benzenesulfonyl)-pyrrolidine-2-carboxylic acid (3-cyano-phenyl)-amide | 0.73; 386.2 | 994 | 98 |
| 26 | (S)-1-(4-Methoxy-benzenesulfonyl)-pyrrolidine-2-carboxylic acid (3,5-dimethyl-phenyl)-amide | 0.83; 389.3 | 30 *2 | 5 *2 |
| 27 | (S)-1-(4-Methoxy-benzenesulfonyl)-pyrrolidine-2-carboxylic acid (3,5-dimethoxy-phenyl)-amide | 0.76; 421.3 | 121 | 16 |
| 28 | (S)-1-(4-Methoxy-benzenesulfonyl)-pyrrolidine-2-carboxylic acid (2-chloro-5-methyl-phenyl)-amide | 0.86; 409.2 | 305 | 224 |
| 29 | (S)-1-(4-Methoxy-benzenesulfonyl)-pyrrolidine-2-carboxylic acid (2-chloro-5-methoxy-phenyl)-amide | 0.83; 425.2 | 625 | 128 |
| 30 | (S)-1-(4-Methoxy-benzenesulfonyl)-pyrrolidine-2-carboxylic acid (3,5-bis-trifluoromethyl-phenyl)-amide | 0.93; 497.2 | 86 | 68 |
| 31 | (S)-1-(4-Methoxy-benzenesulfonyl)-pyrrolidine-2-carboxylic acid (3-chloro-4-fluoro-phenyl)-amide | 0.82; 413.2 | 74 | 34 |
| 32 | (S)-1-(4-Methoxy-benzenesulfonyl)-pyrrolidine-2-carboxylic acid (3-ethoxy-phenyl)-amide | 0.79; 405.3 | 134 | 38 |
| 33 | (S)-1-(4-Methoxy-benzenesulfonyl)-pyrrolidine-2-carboxylic acid indan-5-ylamide | 0.84; 401.3 | 129 *2 | 12 *2 |
| 34 | (S)-1-(4-Methoxy-benzenesulfonyl)-pyrrolidine-2-carboxylic acid (3-ethyl-phenyl)-amide | 0.83; 389.3 | 54 *2 | 8 *2 |
| 35 | (S)-1-(4-Methoxy-benzenesulfonyl)-pyrrolidine-2-carboxylic acid (5-chloro-2-methoxy-phenyl)-amide | 0.86; 425.2 | 714 | 209 |
| 36 | (S)-1-(4-Methoxy-benzenesulfonyl)-pyrrolidine-2-carboxylic acid (3,4-difluoro-phenyl)-amide | 0.79; 397.2 | 569 | 136 |
| 37 | (S)-1-(4-Methoxy-benzenesulfonyl)-pyrrolidine-2-carboxylic acid (4-fluoro-3-methyl-phenyl)-amide | 0.80; 393.3 | 70 | 28 |
| 38 | (S)-1-(4-Methoxy-benzenesulfonyl)-pyrrolidine-2-carboxylic acid (2-fluoro-5-methyl-phenyl)-amide | 0.81; 393.2 | 304 | 26 |
| 39 | (S)-1-(4-Methoxy-benzenesulfonyl)-pyrrolidine-2-carboxylic acid (4-chloro-3-methyl-phenyl)-amide | 0.85; 409.2 | 235 | 18 |
| 40 | (S)-1-(4-Methoxy-benzenesulfonyl)-pyrrolidine-2-carboxylic acid (3,4-dichloro-phenyl)-amide | 0.88; 429.2 | 130 | 58 |
| 41 | (S)-1-(4-Bromo-benzenesulfonyl)-pyrrolidine-2-carboxylic acid (3,5-dimethyl-phenyl)-amide | 0.89; 437.1 | 79 *2 # | 49 *2 # |
| 42 | (S)-1-(Naphthalene-1-sulfonyl)-pyrrolidine-2-carboxylic acid (3,5-dimethyl-phenyl)-amide | 0.90; 409.3 | 216 # | 26 # |
| 43 | (S)-1-(Naphthalene-2-sulfonyl)-pyrrolidine-2-carboxylic acid (3,5-dimethyl-phenyl)-amide | 0.90; 409.3 | 73 # | 25 # |
| 44 | (S)-1-(3,4-Dimethoxy-benzenesulfonyl)-pyrrolidine-2-carboxylic acid (3,5-dimethyl-phenyl)-amide | 0.80; 419.3 | 109 # | 101 # |
| 45 | (S)-1-(2-Methoxy-4-methyl-benzenesulfonyl)-pyrrolidine-2-carboxylic acid (3,5-dimethyl-phenyl)-amide | 0.86; 403.3 | 166 # | 168 # |
| 46 | (S)-1-(4-Chloro-benzenesulfonyl)-pyrrolidine-2-carboxylic acid (3,5-dimethyl-phenyl)-amide | 0.88; 393.2 | 35 *2 # | 32 *2 # |
| 47 | (S)-1-(4-Vinyl-benzenesulfonyl)-pyrrolidine-2-carboxylic acid (3,5-dimethyl-phenyl)-amide | 0.88; 385.3 | 189 *5 # | 92 *5 # |

TABLE 1-continued

Example compounds and characterization

| Example No | Chemical Name | LC-MS $t_R$ in min; $[M + H]^+$ | $IC_{50}Ox1$ [nM] | $IC_{50}Ox2$ [nM] |
|---|---|---|---|---|
| 48 | (S)-1-(2-Methoxy-5-methyl-benzenesulfonyl)-pyrrolidine-2-carboxylic acid (3,5-dimethyl-phenyl)-amide | 0.86; 403.3 | 43 *2 # | 4 *2 # |
| 49 | (S)-1-(4-Methanesulfonyl-benzenesulfonyl)-pyrrolidine-2-carboxylic acid (3,5-dimethyl-phenyl)-amide | 0.75; 437.2 | 16 *2 # | 197 *2 # |
| 50 | (S)-1-(2-Chloro-5-trifluoromethyl-benzenesulfonyl)-pyrrolidine-2-carboxylic acid (3,5-dimethyl-phenyl)-amide | 0.92; 461.2 | 1578 *2 # | 36 *2 # |
| 51 | (S)-1-(2-Chloro-4-trifluoromethyl-benzenesulfonyl)-pyrrolidine-2-carboxylic acid (3,5-dimethyl-phenyl)-amide | 0.93; 461.2 | 80 # | 14 # |
| 52 | (S)-1-(2-Bromo-4-methyl-benzenesulfonyl)-pyrrolidine-2-carboxylic acid (3,5-dimethyl-phenyl)-amide | 0.90; 451.2 | 89 *2 # | 82 *2 # |
| 53 | (S)-1-(4-Chloro-3-trifluoromethyl-benzenesulfonyl)-pyrrolidine-2-carboxylic acid (3,5-dimethyl-phenyl)-amide | 0.95; 461.2 | 48 *2 # | 19 *2 # |
| 54 | (S)-1-(3,4-Dichloro-benzenesulfonyl)-pyrrolidine-2-carboxylic acid (3,5-dimethyl-phenyl)-amide | 0.94; 427.2 | 218 # | 158 # |
| 55 | (S)-1-(4-Chloro-2,5-dimethyl-benzenesulfonyl)-pyrrolidine-2-carboxylic acid (3,5-dimethyl-phenyl)-amide | 0.96; 421.3 | 234 *2 # | 171 *2 # |
| 56 | (S)-1-(2,4-Dimethyl-benzenesulfonyl)-pyrrolidine-2-carboxylic acid (3,5-dimethyl-phenyl)-amide | 0.89; 387.3 | 211 # | 108 # |
| 57 | (S)-1-(4-Bromo-2-methyl-benzenesulfonyl)-pyrrolidine-2-carboxylic acid (3,5-dimethyl-phenyl)-amide | 0.93; 451.2 | 62 # | 22 # |
| 58 | (S)-1-(4-Bromo-2-chloro-benzenesulfonyl)-pyrrolidine-2-carboxylic acid (3,5-dimethyl-phenyl)-amide | 0.93; 471.2 | 179 *2 # | 106 *2 # |
| Ref. Example | (R)-1-(4-Methoxy-benzenesulfonyl)-pyrrolidine-2-carboxylic acid (3,5-dimethyl-phenyl)-amide (prepared in analogy from the corresponding D-proline starting material) | 0.84; 388.9 | 6215 # | 6044 # |

*2 geometric mean of: n = 2 values;
*3 of n = 3 values;
*5 of n = 5 values
$IC_{50}$ values measured using a compound incubation time of 120 min.

II. Biological Assays

1) Sedative Effects: EEG, EMG and Behavioural Indices of Alertness Recorded by Radiotelemetry In Vivo in Wistar Rats.

Electroencephalography (EEG) and Electromyography (EMG) signals were measured by telemetry using TL11M2-F20-EET miniature radiotelemetric implants (Data Science Int.) with two pairs of differential leads.

Surgical implantation was performed under general anesthesia with Ketamin/Xylazin, for cranial placement of one differential pair of EEG electrodes and one pair of EMG leads inserted in either side of the muscles of the neck. After surgery, rats recovered in a thermoregulated chamber and received analgesic treatment with subcutaneous buprenorphine twice a day for 2 d. They were then housed individually and allowed to recover for a minimum of 2 weeks. Thereafter, rats—in their home cage—were placed in a ventilated sound-attenuating box, on a 12-h light/12-h dark cycle, for acclimatization before continuous EEG/EMG recordings started. The telemetric technology that we used in this study allows accurate and stress-free acquisition of biosignals in rats placed in their familiar home cage environment, with no recording leads restricting their movements. Variables analyzed included four different stages of vigilance and sleep, spontaneous activity in the home cage and body temperature. Sleep and wake stages were evaluated using a rodent scoring software (Somnologica Science) directly processing electrical biosignals on 10 s contiguous epochs. The scoring is based on frequency estimation for EEG and amplitude discrimination for EMG and locomotor activity. Using these measurements, the software determines the probability that all components within each epoch best represent active waking (AW), quiet waking (QW), non-REM-sleep (NREM) or REM-sleep (REM). The percentage of total time spent in AW, QW, NREM- and REM-sleep was calculated per 12 h light or dark period. The latency to the onset of the first significant NREM- and REM-sleep episodes and the frequency and duration of those episodes were also calculated. AW, QW, NREM- and REM-sleep, home cage activity and body temperature were measured at baseline for at least one total circadian cycle (12 h-night, 12 h-day) before a test compound was administered. If baseline measurements indicated that animals were stable, test compound or vehicle was given in the evening by oral gavage at the end of the baseline 12-h day period, immediately before the nocturnal rise in orexin and activity in rats. All variables were subsequently recorded for 12 h following administration of the orexin receptor antagonist.

The compound of Example 26 has been tested in this assay (oral dosage: 100 mg/kg po; effects analyzed over 6 hours): Results are: −26% on active wake, −51% on home cage activity, +28% on NREM sleep, +69% on REM sleep; when compared to vehicle controls.

2) Effects on Morphine-Induced Locomotor Sensitization

Principle:

Repeated administration of psychostimulants or opiates across various species including rodents causes the development of "reverse tolerance" known as sensitization. The term sensitization refers to an increase in a response (here locomotion) after the repeated occurrence of the stimulus (drug administration) that promoted the aforementioned response.

The increased sensitivity to the locomotor stimulating effect of such drugs (behavioural sensitization) is believed to be relevant to the psychopathology, neurotoxicity, addiction and to the craving that develop in humans abusing psychostimulants or opiates [Vanderschuren L J M J et al., in Self D W, Staley J K (eds.) "Behavioral Neuroscience of Drug Addiction", Current Topics in Behavioral Neurosciences 3 (2009), 179-195].

Sensitization to the locomotor effects of drugs of abuse is believed to reflect sensitization to the rewarding effects of these agents. For instance, previous drug experience has been reported to increase the probability that animals will self-administer the drug later on. Thus, it is hypothesized that the extent to which sensitization to the rewarding effects of morphine develops in rats may reflect the extent of drug craving and reinstatement of compulsive drug-seeking behavior in humans. Compounds which are effective in such model may have beneficial effects in treating drug substance addicts (here: opiate addicts) by attenuating their drug craving (i.e., the "wanting" of the drug) and thereby reducing their likeliness towards later relapse of drug-seeking behavior.

Method:

16 male Sprague Dawley rats were injected with morphine (10 mg/kg i.p.) and placed immediately afterwards in an open field arena for 45 min. Total distance moved (in cm) was recorded via video-tracking. This procedure was repeated 4 times until robust locomotor sensitization had developed. Two hours before the $5^{th}$ injection of morphine, the compound of example 26 was orally administered at a dose of 100 mg/kg. Finally, one day later, rats were again injected with morphine for the $6^{th}$ time without receiving pre-treatment.

Morphine injected rats developed pronounced locomotor sensitization [i.e., their total distance moved after the third and fourth morphine injection (columns 3 and 4) was significantly greater than after the first injection (column 1)]. Pre-treatment with the compound of example 26 completely abolished the locomotor sensitization in response to the $5^{th}$ injection of morphine (column 5). This effect was not due to a potential naturally occurring time-dependent decrease of sensitization as the $6^{th}$ morphine injection (column 6), given a day later, restored locomotor sensitization to levels observed at the fourth injection (FIG. 1: Effects of compound of example 26 on morphine-induced locomotor sensitization).

3) Effects on Social Stress-Induced Hyperthermia and Tachycardia

Principle:

Exposure to both physiological and psychological stress in mammals leads to an elevation of core body temperature and heart rate referred to as stress-induced hyperthermia (SIH) and stress-induced tachycardia (SIT). Both responses are due to an activation of the autonomous nervous system by stress, and the SIH/SIT paradigm possesses excellent animal-to-human translational properties. The SIH model in rodents has undergone extensive pharmacological testing and was shown to be sensitive to the action of a variety of clinically effective anxiolytic drugs [Vinkers C H et al., European J Pharmacol. 2008, 585, 407-425].

The SIH/SIT response can be observed in humans equally well as in rodents providing excellent animal to human translational possibilities. Although the SIH/SIT response can be evoked by different kinds of stress, the use of social interaction as stressor in rats in the current study may suggest a particular potential of the test compound for the treatment of psychiatric disorders in humans associated with increased autonomous nervous system responses to emotional stress.

Figure 2:
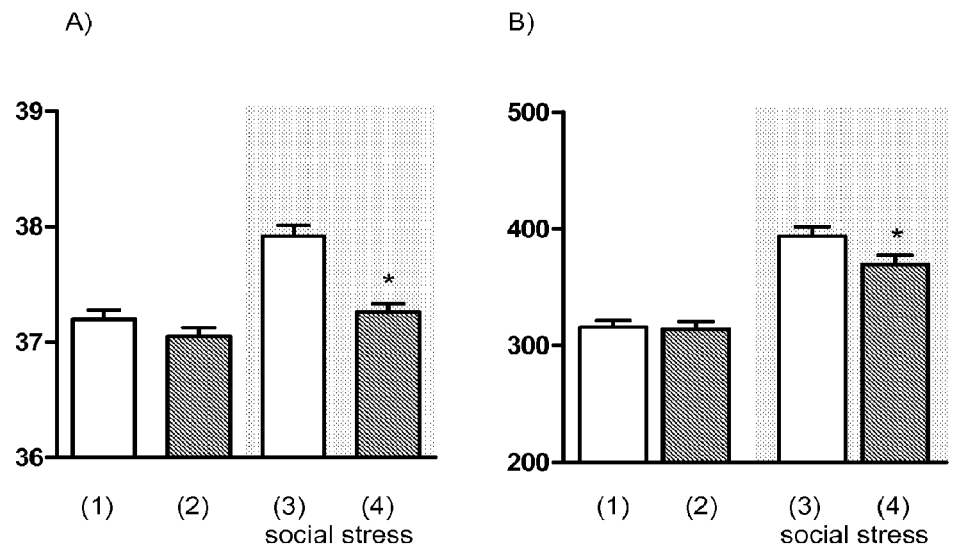
FIG. 2 shows the effects of the compound of example 26 on social stress-induced hyperthermia and tachycardia.

Method:

12 male Wistar rats were implanted intraperitoneally with transmitters that allowed the simultaneous recording of body temperature (in degrees Celsius) [FIG. 2 A)] and heart rate (in beats per minute) [FIG. 2 B)] via external receivers. Rats were treated orally with 100 mg/kg of compound of example 26 two hours before exposure to an one hour-lasting social interaction stress. Columns 1 and 2 show the effect on body temperature [FIG. 2 A)], respectively heart rate [FIG. 2 B)], after vehicle (1) or drug (2) treatment without exposure to stress; columns 3 and 4 show the effect with exposure to stress after vehicle (3) or drug (4) treatment.

Compound of example 26 significantly attenuated social stress-induced hyperthermia and tachycardia without affecting baseline body temperature and heart rate during the $2^{nd}$ hour after treatment (FIG. 2: Effects of compound of example 26 on social stress-induced hyperthermia and tachycardia).

4) Effects of Compound of Example 26 on Fear-Potentiated Startle

Principle:

The fear-potentiated startle (FPS) paradigm is a model of conditioned fear [Fendt M et al., Neuroscience Biobehav Rev. 1999, 23, 743-760]. Rats can be trained to associate an initially neutral, soon-to-be conditioned stimulus (CS; e.g., light) with an aversive, unconditioned stimulus (US; e.g., foot shock). When tested after training for their startle reflex response to brief (ms) noise bursts in the absence (no-CS) vs. the presence of the CS, rats generally show greater startle amplitudes during the presence of the CS which now serves as a predictor of shock. In humans a similar training procedure can be implemented and a FPS response can also be evoked in the presence of a shock-predicting CS.

Conditioned fear models including FPS mimic in particular the response to specific threats. Therefore, a potential anxiolytic effect of a compound as revealed in the FPS paradigm may prove particularly beneficial for phobias or anxiety-disorders associated with a defined traumatic event such as post-traumatic stress disorder. A lack of myorelaxant effects of a compound suggests that the reductions of startle responses under no-CS conditions are not due to impaired muscle tonus. Rather the compound may reduce those startle reactions as a consequence of reduced fear of the shock-context or reduced fear of the slightly aversive startle-eliciting noise pulses per se.

Method:

Male F344 rats were trained for two consecutive days (conditioning phase) to associate a light-stimulus with a foot shock. On the following day they were tested for their response to startle-eliciting noise stimuli which were delivered randomly under light (CS) or dark (no-CS) conditions. Two hours before the test rats were treated with one dose of compound of example 26 (0, 30, 100, 300 mg/kg p.o.). Average startle responses under light (CS) [FIG. 3 A)] and dark conditions (no-CS) [FIG. 3 B)] during the test day were measured and recorded as an electric signal (in mV). Following startle testing, rats underwent an additional forepaw grip strength (in g) [FIG. 3 C)] test to control for potential myorelaxant effects of the compound (dosed at 0, 30, 100, 300 mg/kg p.o.).

Figure 3:
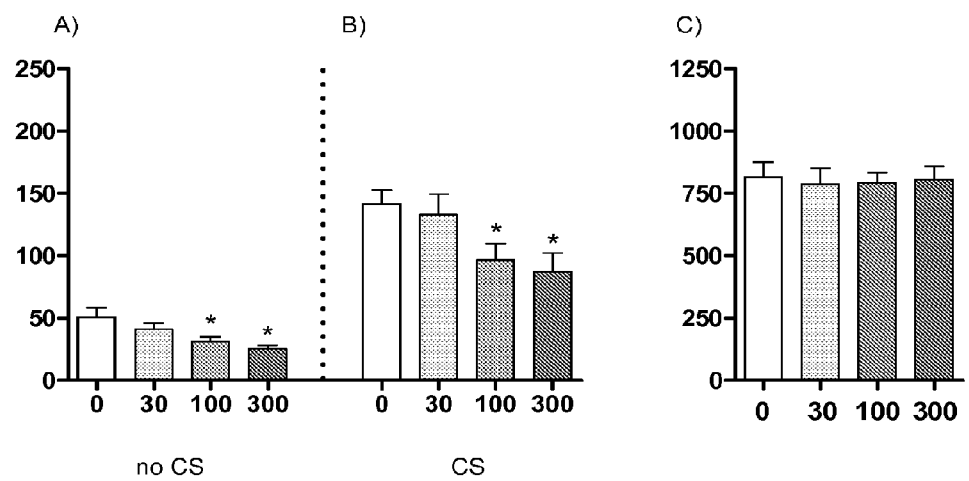
FIG. 3 shows the effects of the compound of example 26 on fear-potentiated startle and grip strength.

Compound of example 26 at doses of 100 and 300 mg/kg significantly reduced the fear-potentiated startle response under CS and under no-CS conditions without affecting grip strength (FIG. 3: Effects of compound of example 26 on fear-potentiated startle and grip strength).

The invention claimed is:

1. A method for antagonizing an orexin receptor in a subject having an anxiety disorder, comprising administering to said subject a pharmaceutical composition comprising the compound (S)-1-(4-Methoxy-benzenesulfonyl)-pyrrolidine-2-carboxylic acid (3,5-dimethyl-phenyl)-amide.

2. A method according to claim 1, wherein said anxiety disorder is selected from a phobic anxiety or a post-traumatic stress disorder.

3. A method according to claim 1, wherein said pharmaceutical composition comprises a pharmaceutically acceptable carrier.

4. A method according to claim 2, wherein said pharmaceutical composition comprises a pharmaceutically acceptable carrier.

5. A method according to claim 3, wherein said compound is (S)-1-(4-Methoxy-benzenesulfonyl)-pyrrolidine-2-carboxylic acid (3,5-dimethyl-phenyl)-amide in free form.

6. A method according to claim 4, wherein said compound is (S)-1-(4-Methoxy-benzenesulfonyl)-pyrrolidine-2-carboxylic acid (3,5-dimethyl-phenyl)-amide in free form.

7. A method according to claim 2, wherein said anxiety disorder is a phobic anxiety.

8. A method according to claim 2, wherein said anxiety disorder is a post-traumatic stress disorder.

9. A method according to claim 4, wherein said anxiety disorder a phobic anxiety.

10. A method according to claim 4, wherein said anxiety disorder is a post-traumatic stress disorder.

11. A method according to claim 6, wherein said anxiety disorder is a phobic anxiety.

12. A method according to claim 6, wherein said anxiety disorder is a post-traumatic stress disorder.

13. A method according to claim 1, wherein said anxiety disorder is a circumscribed threat induced anxiety disorder.

* * * * *